US009080164B2

(12) United States Patent
Kurihara et al.

(10) Patent No.: US 9,080,164 B2
(45) Date of Patent: Jul. 14, 2015

(54) MUTANT β-GLUCOSIDASE, ENZYME COMPOSITION FOR DECOMPOSING BIOMASS, AND METHOD OF PRODUCING SUGAR SOLUTION

(71) Applicant: Toray Industries, Inc., Tokyo (JP)

(72) Inventors: Hiroyuki Kurihara, Kanagawa (JP); Katsushige Yamada, Kanagawa (JP); Kazuhiko Ishikawa, Hiroshima (JP); Yumiko Mishima, Hiroshima (JP); Yasunobu Wada, Osaka (JP); Yuji Kado, Osaka (JP)

(73) Assignee: Toray Industries, Inc. (JP)

(*) Notice: Subject to any disclaimer, the term of this patent is extended or adjusted under 35 U.S.C. 154(b) by 0 days.

(21) Appl. No.: 14/154,547

(22) Filed: Jan. 14, 2014

(65) Prior Publication Data

US 2014/0127759 A1 May 8, 2014

Related U.S. Application Data

(63) Continuation of application No. PCT/JP2012/050539, filed on Jan. 13, 2012.

(30) Foreign Application Priority Data

Jul. 14, 2011 (JP) ................................. 2011-155792

(51) Int. Cl.
*C12P 19/14* (2006.01)
*C12N 9/42* (2006.01)
*C12P 19/02* (2006.01)

(52) U.S. Cl.
CPC ............... *C12N 9/2445* (2013.01); *C12P 19/02* (2013.01); *C12P 19/14* (2013.01); *C12Y 302/01021* (2013.01)

(58) Field of Classification Search
None
See application file for complete search history.

(56) References Cited

FOREIGN PATENT DOCUMENTS

| JP | 2011-024501 A | 2/2011 |
|---|---|---|
| JP | 2012-034690 A | 2/2012 |

OTHER PUBLICATIONS

Servé W.M. Kengen et al., "Purification and characterization of an extremely thermostable β-glucosidase from the hyperthermophilic archaeon *Pyrococcus furiosus*," European Journal of Biochemistry, vol. 213, Issue 1, pp. 305-312, Apr. 1993 (Abstract only).

Hideki Ohba et al., "Improvement of the Thermostability of Pyruvate Decarboxylase by Modifcation with an Amylose Derivative," *Biosci. Biotech. Biochem*., vol. 59, No. 8, pp. 1581-1583, 1995.

W.G. Voorhorst et al., "Characterization of the celB gene coding for beta-glucosidase from the hyperthermophilic archaeon *Pyrococcus furiosus* and its expression and site-directed mutation in *Escherichia coli*," J. Bacteriol., vol. 177, No. 24, pp. 7105-7111, Dec. 1995 (Abstract only).

Michael W. Bauer et al., "Comparison of a β-Glucosidase and a β-Mannosidase from the Hyperthermophilic Archaeon *Pyrococcus furiosus*," The Journal of Biological Chemistry, vol. 271, No. 39, pp. 23749-23755, Sep. 27, 1996.

G. Palamarczyk et al., "Protein secretion and glycosylation in *Trichoderma,*" *Trichoderma* and *Gliocladium*: Basic biology, taxonomy and genetics, vol. 1, pp. 121-138, 1998, edited by Christian P. Kubicek et al.

Joyce H.G. Lebbink et al., "Improving Low-Temperature Catalysis in the Hyperthermotable *Pryococcus furiosus* β-Glucosidase CelB by Directed Evolution," Biochemistry, vol. 39, No. 13, pp. 3656-3665, 2000.

Thijs Kaper et al., "Comparative Structural Analysis and Substrate Specificity Engineering of the Hyperthermostable β-Glucosidase CelB from *Pyrococcus furiosus*," Biochemistry, vol. 39, No. 17, pp. 4963-4970, 2000 (Abstract only).

Fabrizio Gentile et al., "SDS-resistant Active and Thermostable Dimers Are Obtained from the Dissociation of Homotetrameric β-Glycosidase from Hyperthermophilic *Sulfolobus solfataricus* in SDS," J. Biol. Chem., vol. 277, No. 46, pp. 44050-44060, Nov. 15, 2002.

Hetti Palonen et al., "Adsorption of *Trichoderma reesei* CHB I and EG II and their catalytic domains on steam pretreated softwood and isolated lignin," Journal of Biotechnology, vol. 107, pp. 65-72, 2004.

Y. Kado et al., "Structure of hyperthermophilic β-glucosidase from *Pyrococcus furiosus*," Acta Cryst., Section F, vol. 67, pp. 1473-1479, 2011 (Abstract only).

Yumiko Mishima, et al., "Analysis of Structure and Function of Superheat-Resistant β-Glucosidase," *Japan Society for Bioscience, Biotechnology, and Agrochemistry*, Mar. 5, 2011, vol. 2011, p. 12.

European Search Report dated Feb. 20, 2015.

"Archaebacterium AEPILLa endoglucanase", XP002735627, retrieved from EBI accession No. GSP:AAW34994, Database accession No. AAW34994 *sequence*, May 21, 1998.

*Primary Examiner* — Nashaat Nashed
(74) *Attorney, Agent, or Firm* — DLA Piper LLP (US)

(57) ABSTRACT

A β-glucosidase exhibits high activity in the presence of biomass and has high thermal stability compared to conventional enzymes. The β-glucosidase includes substitutions and/or deletions of amino acids, at least three amino acids selected from the group consisting of Glu39, Asp169, Arg170, Arg220, Tyr227, and Glu330, of the parent β-glucosidase with other amino acids and exhibits a decomposition activity.

12 Claims, 5 Drawing Sheets

Column: Superdex200
Buffer: 50mM Tris-HCl pH8.0, 150mM NaCl
Flow rate: 2 mL/min
Mutant glucosidase (R170A/R220A/R227F/R448G)
Mutant glucosidase (R170A/R220A/R227F/R448E)
Mutant glucosidase (R170A/R220A/R227F/R459G)
Mutant glucosidase (R170A/R220A/R227F/E449R)
Mutant glucosidase (R170A/R220A/R227F)
Parent glucosidase
A280(mAU)
1800.00
1600.00
1400.00
1200.00
1000.00
800.00
600.00
400.00
200.00
0.00
-200.00
30
50
70
90
110
130
150
170
190
210
230
250
vol.(ml)

SEQUENCE LISTING

```
<160> NUMBER OF SEQ ID NOS: 38

<210> SEQ ID NO 1
<211> LENGTH: 472
<212> TYPE: PRT
<213> ORGANISM: Pyrococcus furiosus

<400> SEQUENCE: 1

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Arg Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Arg Ser Gly Phe Pro
    210                 215                 220

Pro Gly Tyr Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270
```

```
Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 2
<211> LENGTH: 1416
<212> TYPE: DNA
<213> ORGANISM: Pyrococcus furiosus

<400> SEQUENCE: 2

gcaaagttcc caaaaaactt catgtttgga tattcttggt ctggtttcca gtttgagatg      60

ggactgccag gaagtgaagt ggaaagcgac tggtgggtgt gggttcacga caaggagaac     120

atagcatcag gtctagtaag tggagatcta ccagagaacg gcccagcata ttggcacctc     180

tataagcaag atcatgacat tgcagaaaag ctaggaatgg attgtattag aggtggcatt     240

gagtgggcaa gaatttttcc aaagccaaca tttgacgtta aagttgatgt ggaaaaggat     300

gaagaaggca acataatttc cgtagacgtt ccagagagta caataaaaga gctagagaaa     360

attgccaaca tggaggccct tgaacattat cgcaagattt actcagactg gaaggagagg     420

ggcaaaacct tcatattaaa cctctaccac tggcctcttc cattatggat tcatgaccca     480

attgcagtaa ggaaacttgg cccggatagg gctcctgcag gatggttaga tgagaagaca     540

gtggtagagt ttgtgaagtt tgccgccttc gttgcttatc accttgatga cctcgttgac     600

atgtggagca caatgaacga accaaacgta gtctacaatc aaggttacat taatctacgt     660

tcaggatttc caccaggata tctaagcttt gaagcagcag aaaaggcaaa attcaactta     720

attcaggctc acatcggagc atatgatgcc ataaaagagt attcagaaaa atccgtggga     780

gtgatatacg cctttgcttg gcacgatcct ctagcggagg agtataagga tgaagtagag     840

gaaatcagaa agaaagacta tgagtttgta acaattctac actcaaaagg aaagctagac     900

tggatcggcg taaactacta ctccaggctg gtatatggag ccaaagatgg acacctagtt     960
```

```
cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cagagaaata gccactcaaa aagaaattcc agaagaatta   1380

gctcacctcg cagacctcaa atttgttaca agaaag                             1416


<210> SEQ ID NO 3
<211> LENGTH: 40
<212> TYPE: DNA
<213> ORGANISM: Artificial
<220> FEATURE:
<223> OTHER INFORMATION: primer

<400> SEQUENCE: 3

caattgcagt aaggaaactt ggcccggatg cggctcctgc                           40


<210> SEQ ID NO 4
<211> LENGTH: 40
<212> TYPE: DNA
<213> ORGANISM: Artificial
<220> FEATURE:
<223> OTHER INFORMATION: primer

<400> SEQUENCE: 4

gcaggagccg catccgggcc aagtttcctt actgcaattg                           40


<210> SEQ ID NO 5
<211> LENGTH: 35
<212> TYPE: DNA
<213> ORGANISM: Artificial
<220> FEATURE:
<223> OTHER INFORMATION: primer

<400> SEQUENCE: 5

ggttacatta atctagcttc aggatttcca ccagg                                35


<210> SEQ ID NO 6
<211> LENGTH: 35
<212> TYPE: DNA
<213> ORGANISM: Artificial
<220> FEATURE:
<223> OTHER INFORMATION: primer

<400> SEQUENCE: 6

cctggtggaa atcctgaagc tagattaatg taacc                                35


<210> SEQ ID NO 7
<211> LENGTH: 32
<212> TYPE: DNA
<213> ORGANISM: Artificial
<220> FEATURE:
<223> OTHER INFORMATION: primer

<400> SEQUENCE: 7

ggatttccac caggatttct aagctttgaa gc                                   32


<210> SEQ ID NO 8
<211> LENGTH: 32
```

```
<212> TYPE: DNA
<213> ORGANISM: Artificial
<220> FEATURE:
<223> OTHER INFORMATION: primer

<400> SEQUENCE: 8

gcttcaaagc ttagaaatcc tggtggaaat cc                                    32


<210> SEQ ID NO 9
<211> LENGTH: 472
<212> TYPE: PRT
<213> ORGANISM: Pyrococcus furiosus R170A

<400> SEQUENCE: 9

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Arg Ser Gly Phe Pro
    210                 215                 220

Pro Gly Tyr Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335
```

```
Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 10
<211> LENGTH: 472
<212> TYPE: PRT
<213> ORGANISM: Pyrococcus furiosus R220A

<400> SEQUENCE: 10

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Arg Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Tyr Leu Ser Phe Glu Ala Ala Glu Lys Ala Lys Phe Asn Leu
```

```
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 11
<211> LENGTH: 472
<212> TYPE: PRT
<213> ORGANISM: Pyrococcus furiosus Y227F

<400> SEQUENCE: 11

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125
```

```
His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Arg Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Arg Ser Gly Phe Pro
    210                 215                 220

Pro Gly Phe Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 12
<211> LENGTH: 472
<212> TYPE: PRT
<213> ORGANISM: Pyrococcus furiosus R170A/Y227F

<400> SEQUENCE: 12

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30
```

```
Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Arg Ser Gly Phe Pro
    210                 215                 220

Pro Gly Phe Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445
```

```
Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 13
<211> LENGTH: 472
<212> TYPE: PRT
<213> ORGANISM: Pyrococcus furiosus R170A/R220A

<400> SEQUENCE: 13

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Tyr Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350
```

```
Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 14
<211> LENGTH: 472
<212> TYPE: PRT
<213> ORGANISM: Pyrococcus furiosus R170A/R220A/Y227F

<400> SEQUENCE: 14

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Phe Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
```

```
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 15
<211> LENGTH: 472
<212> TYPE: PRT
<213> ORGANISM: Pyrococcus furiosus R170A/R220A/Y227F(with glycosilation
      site)

<400> SEQUENCE: 15

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp Asn Arg Thr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140
```

```
Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Phe Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470
```

<210> SEQ ID NO 16
<211> LENGTH: 1380
<212> TYPE: DNA
<213> ORGANISM: Pyrococcus furiosus R170A

<400> SEQUENCE: 16

```
gcaaagttcc caaaaaactt catgtttgga tattcttggt ctggtttcca gtttgagatg      60

ggactgccag gaagtgaagt ggaaagcgac tggtgggtgt gggttcacga caaggagaac     120

atagcatcag gtctagtaag tggagatcta ccagagaacg gcccagcata ttggcacctc     180

tataagcaag atcatgacat tgcagaaaag ctaggaatgg attgtattag aggtggcatt     240
```

```
gagtgggcaa gaatttttcc aaagccaaca tttgacgtta aagttgatgt ggaaaaggat    300
gaagaaggca acataatttc cgtagacgtt ccagagagta caataaaaga gctagagaaa    360
attgccaaca tggaggccct tgaacattat cgcaagattt actcagactg gaaggagagg    420
ggcaaaacct tcatattaaa cctctaccac tggcctcttc cattatggat tcatgaccca    480
attgcagtaa ggaaacttgg cccggatgcg gctcctgcag gatggttaga tgagaagaca    540
gtggtagagt ttgtgaagtt tgccgccttc gttgcttatc accttgatga cctcgttgac    600
atgtggagca caatgaacga accaaacgta gtctacaatc aaggttacat taatctacgt    660
tcaggatttc caccaggata tctaagcttt gaagcagcag aaaaggcaaa attcaactta    720
attcaggctc acatcggagc atatgatgcc ataaaagagt attcagaaaa atccgtggga    780
gtgatatacg cctttgcttg gcacgatcct ctagcggagg agtataagga tgaagtagag    840
gaaatcagaa agaaagacta tgagtttgta acaattctac actcaaaagg aaagctagac    900
tggatcggcg taaactacta ctccaggctg gtatatggag ccaaagatgg acacctagtt    960
cctttacctg gatatggatt tatgagtgag agaggaggat ttgcaaagtc aggaagacct   1020
gctagtgact ttggatggga aatgtaccca gagggccttg agaaccttct taagtattta   1080
aacaatgcct acgagctacc aatgataatt acagagaacg gtatggccga tgcagcagat   1140
agatacaggc cacactatct cgtaagccat ctaaaggcag tttacaatgc tatgaaagaa   1200
ggtgctgatg ttagagggta tctccactgg tctctaacag acaactacga atgggcccaa   1260
gggttcagga tgagatttgg attggtttac gtggatttcg agacaaagaa gagatattta   1320
aggccaagcg ccctggtatt cagagaaata gccactcaaa aagaaattcc agaagaatta   1380
```

<210> SEQ ID NO 17
<211> LENGTH: 1416
<212> TYPE: DNA
<213> ORGANISM: Pyrococcus furiosus R220A

<400> SEQUENCE: 17

```
gcaaagttcc caaaaaactt catgtttgga tattcttggt ctggtttcca gtttgagatg     60
ggactgccag gaagtgaagt ggaaagcgac tggtgggtgt gggttcacga caaggagaac    120
atagcatcag gtctagtaag tggagatcta ccagagaacg gcccagcata ttggcacctc    180
tataagcaag atcatgacat tgcagaaaag ctaggaatgg attgtattag aggtggcatt    240
gagtgggcaa gaatttttcc aaagccaaca tttgacgtta aagttgatgt ggaaaaggat    300
gaagaaggca acataatttc cgtagacgtt ccagagagta caataaaaga gctagagaaa    360
attgccaaca tggaggccct tgaacattat cgcaagattt actcagactg gaaggagagg    420
ggcaaaacct tcatattaaa cctctaccac tggcctcttc cattatggat tcatgaccca    480
attgcagtaa ggaaacttgg cccggatagg gctcctgcag gatggttaga tgagaagaca    540
gtggtagagt ttgtgaagtt tgccgccttc gttgcttatc accttgatga cctcgttgac    600
atgtggagca caatgaacga accaaacgta gtctacaatc aaggttacat taatctagct    660
tcaggatttc caccaggata tctaagcttt gaagcagcag aaaaggcaaa attcaactta    720
attcaggctc acatcggagc atatgatgcc ataaaagagt attcagaaaa atccgtggga    780
gtgatatacg cctttgcttg gcacgatcct ctagcggagg agtataagga tgaagtagag    840
gaaatcagaa agaaagacta tgagtttgta acaattctac actcaaaagg aaagctagac    900
tggatcggcg taaactacta ctccaggctg gtatatggag ccaaagatgg acacctagtt    960
```

```
cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cagagaaata gccactcaaa aagaaattcc agaagaatta   1380

gctcacctcg cagacctcaa atttgttaca agaaag                             1416
```

<210> SEQ ID NO 18
<211> LENGTH: 1416
<212> TYPE: DNA
<213> ORGANISM: Pyrococcus furiosus Y227F

<400> SEQUENCE: 18

```
gcaaagttcc caaaaaactt catgtttgga tattcttggt ctggtttcca gtttgagatg     60

ggactgccag gaagtgaagt ggaaagcgac tggtgggtgt gggttcacga caaggagaac    120

atagcatcag gtctagtaag tggagatcta ccagagaacg gcccagcata ttggcacctc    180

tataagcaag atcatgacat tgcagaaaag ctaggaatgg attgtattag aggtggcatt    240

gagtgggcaa gaatttttcc aaagccaaca tttgacgtta aagttgatgt ggaaaaggat    300

gaagaaggca acataatttc cgtagacgtt ccagagagta caataaaaga gctagagaaa    360

attgccaaca tggaggccct tgaacattat cgcaagattt actcagactg gaaggagagg    420

ggcaaaacct tcatattaaa cctctaccac tggcctcttc cattatggat tcatgaccca    480

attgcagtaa ggaaacttgg cccggatagg gctcctgcag gatggttaga tgagaagaca    540

gtggtagagt ttgtgaagtt tgccgccttc gttgcttatc accttgatga cctcgttgac    600

atgtggagca caatgaacga accaaacgta gtctacaatc aaggttacat taatctacgt    660

tcaggatttc caccaggatt tctaagcttt gaagcagcag aaaaggcaaa attcaactta    720

attcaggctc acatcggagc atatgatgcc ataaaagagt attcagaaaa atccgtggga    780

gtgatatacg cctttgcttg gcacgatcct ctagcggagg agtataagga tgaagtagag    840

gaaatcagaa agaaagacta tgagtttgta acaattctac actcaaaagg aaagctagac    900

tggatcggcg taaactacta ctccaggctg gtatatggag ccaaagatgg acacctagtt    960

cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cagagaaata gccactcaaa aagaaattcc agaagaatta   1380

gctcacctcg cagacctcaa atttgttaca agaaag                             1416
```

<210> SEQ ID NO 19
<211> LENGTH: 1416
<212> TYPE: DNA
<213> ORGANISM: Pyrococcus furiosus R170A/Y227F

<400> SEQUENCE: 19

```
gcaaagttcc caaaaaactt catgtttgga tattcttggt ctggtttcca gtttgagatg     60

ggactgccag gaagtgaagt ggaaagcgac tggtgggtgt gggttcacga caaggagaac    120

atagcatcag gtctagtaag tggagatcta ccagagaacg gcccagcata ttggcacctc    180

tataagcaag atcatgacat tgcagaaaag ctaggaatgg attgtattag aggtggcatt    240

gagtgggcaa gaatttttcc aaagccaaca tttgacgtta aagttgatgt ggaaaaggat    300

gaagaaggca acataatttc cgtagacgtt ccagagagta caataaaaga gctagagaaa    360

attgccaaca tggaggccct tgaacattat cgcaagattt actcagactg gaaggagagg    420

ggcaaaacct tcatattaaa cctctaccac tggcctcttc cattatggat tcatgaccca    480

attgcagtaa ggaaacttgg cccggatgcg gctcctgcag gatggttaga tgagaagaca    540

gtggtagagt ttgtgaagtt tgccgccttc gttgcttatc accttgatga cctcgttgac    600

atgtggagca caatgaacga accaaacgta gtctacaatc aaggttacat taatctacgt    660

tcaggatttc caccaggatt tctaagcttt gaagcagcag aaaaggcaaa attcaactta    720

attcaggctc acatcggagc atatgatgcc ataaaagagt attcagaaaa atccgtggga    780

gtgatatacg cctttgcttg gcacgatcct ctagcggagg agtataagga tgaagtagag    840

gaaatcagaa agaaagacta tgagtttgta acaattctac actcaaaagg aaagctagac    900

tggatcggcg taaactacta ctccaggctg gtatatggag ccaaagatgg acacctagtt    960

cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cagagaaata gccactcaaa aagaaattcc agaagaatta   1380

gctcacctcg cagacctcaa atttgttaca agaaag                             1416
```

```
<210> SEQ ID NO 20
<211> LENGTH: 1416
<212> TYPE: DNA
<213> ORGANISM: Pyrococcus furiosus R170A/R220A/Y227F

<400> SEQUENCE: 20
```

```
gcaaagttcc caaaaaactt catgtttgga tattcttggt ctggtttcca gtttgagatg     60

ggactgccag gaagtgaagt ggaaagcgac tggtgggtgt gggttcacga caaggagaac    120

atagcatcag gtctagtaag tggagatcta ccagagaacg gcccagcata ttggcacctc    180

tataagcaag atcatgacat tgcagaaaag ctaggaatgg attgtattag aggtggcatt    240

gagtgggcaa gaatttttcc aaagccaaca tttgacgtta aagttgatgt ggaaaaggat    300

gaagaaggca acataatttc cgtagacgtt ccagagagta caataaaaga gctagagaaa    360

attgccaaca tggaggccct tgaacattat cgcaagattt actcagactg gaaggagagg    420

ggcaaaacct tcatattaaa cctctaccac tggcctcttc cattatggat tcatgaccca    480

attgcagtaa ggaaacttgg cccggatgcg gctcctgcag gatggttaga tgagaagaca    540

gtggtagagt ttgtgaagtt tgccgccttc gttgcttatc accttgatga cctcgttgac    600

atgtggagca caatgaacga accaaacgta gtctacaatc aaggttacat taatctagct    660
```

```
tcaggatttc caccaggatt tctaagcttt gaagcagcag aaaaggcaaa attcaactta    720

attcaggctc acatcggagc atatgatgcc ataaaagagt attcagaaaa atccgtggga    780

gtgatatacg cctttgcttg gcacgatcct ctagcggagg agtataagga tgaagtagag    840

gaaatcagaa agaaagacta tgagtttgta acaattctac actcaaaagg aaagctagac    900

tggatcggcg taaactacta ctccaggctg gtatatggag ccaaagatgg acacctagtt    960

cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cagagaaata gccactcaaa aagaaattcc agaagaatta   1380

gctcacctcg cagacctcaa atttgttaca agaaag                             1416


<210> SEQ ID NO 21
<211> LENGTH: 1416
<212> TYPE: DNA
<213> ORGANISM: Pyrococcus furiosus R170A/R220A

<400> SEQUENCE: 21

gcaaagttcc caaaaaactt catgtttgga tattcttggt ctggtttcca gtttgagatg     60

ggactgccag gaagtgaagt ggaaagcgac tggtgggtgt gggttcacga caaggagaac    120

atagcatcag gtctagtaag tggagatcta ccagagaacg gcccagcata ttggcacctc    180

tataagcaag atcatgacat tgcagaaaag ctaggaatgg attgtattag aggtggcatt    240

gagtgggcaa gaatttttcc aaagccaaca tttgacgtta aagttgatgt ggaaaaggat    300

gaagaaggca acataatttc cgtagacgtt ccagagagta caataaaaga gctagagaaa    360

attgccaaca tggaggccct tgaacattat cgcaagattt actcagactg gaaggagagg    420

ggcaaaacct tcatattaaa cctctaccac tggcctcttc cattatggat tcatgaccca    480

attgcagtaa ggaaacttgg cccggatgcg gctcctgcag gatggttaga tgagaagaca    540

gtggtagagt ttgtgaagtt tgccgccttc gttgcttatc accttgatga cctcgttgac    600

atgtggagca caatgaacga accaaacgta gtctacaatc aaggttacat taatctagct    660

tcaggatttc caccaggata tctaagcttt gaagcagcag aaaaggcaaa attcaactta    720

attcaggctc acatcggagc atatgatgcc ataaaagagt attcagaaaa atccgtggga    780

gtgatatacg cctttgcttg gcacgatcct ctagcggagg agtataagga tgaagtagag    840

gaaatcagaa agaaagacta tgagtttgta acaattctac actcaaaagg aaagctagac    900

tggatcggcg taaactacta ctccaggctg gtatatggag ccaaagatgg acacctagtt    960

cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cagagaaata gccactcaaa aagaaattcc agaagaatta   1380
```

```
gctcacctcg cagacctcaa atttgttaca agaaag                        1416


<210> SEQ ID NO 22
<211> LENGTH: 481
<212> TYPE: PRT
<213> ORGANISM: Thermosphaera aggregans

<400> SEQUENCE: 22

Met Lys Phe Pro Lys Asp Phe Met Ile Gly Tyr Ser Ser Ser Pro Phe
1               5                   10                  15

Gln Phe Glu Ala Gly Ile Pro Gly Ser Glu Asp Pro Asn Ser Asp Trp
            20                  25                  30

Trp Val Trp Val His Asp Pro Glu Asn Thr Ala Ala Gly Leu Val Ser
        35                  40                  45

Gly Asp Phe Pro Glu Asn Gly Pro Gly Tyr Trp Asn Leu Asn Gln Asn
    50                  55                  60

Asp His Asp Leu Ala Glu Lys Leu Gly Val Asn Thr Ile Arg Val Gly
65                  70                  75                  80

Val Glu Trp Ser Arg Ile Phe Pro Lys Pro Thr Phe Asn Val Lys Val
                85                  90                  95

Pro Val Glu Arg Asp Glu Asn Gly Ser Ile Val His Val Asp Val Asp
            100                 105                 110

Asp Lys Ala Val Glu Arg Leu Asp Glu Leu Ala Asn Lys Glu Ala Val
        115                 120                 125

Asn His Tyr Val Glu Met Tyr Lys Asp Trp Val Glu Arg Gly Arg Lys
    130                 135                 140

Leu Ile Leu Asn Leu Tyr His Trp Pro Leu Pro Leu Trp Leu His Asn
145                 150                 155                 160

Pro Ile Met Val Arg Arg Met Gly Pro Asp Arg Ala Pro Ser Gly Trp
                165                 170                 175

Leu Asn Glu Glu Ser Val Val Glu Phe Ala Lys Tyr Ala Ala Tyr Ile
            180                 185                 190

Ala Trp Lys Met Gly Glu Leu Pro Val Met Trp Ser Thr Met Asn Glu
        195                 200                 205

Pro Asn Val Val Tyr Glu Gln Gly Tyr Met Phe Val Lys Gly Gly Phe
    210                 215                 220

Pro Pro Gly Tyr Leu Ser Leu Glu Ala Ala Asp Lys Ala Arg Arg Asn
225                 230                 235                 240

Met Ile Gln Ala His Ala Arg Ala Tyr Asp Asn Ile Lys Arg Phe Ser
                245                 250                 255

Lys Lys Pro Val Gly Leu Ile Tyr Ala Phe Gln Trp Phe Glu Leu Leu
            260                 265                 270

Glu Gly Pro Ala Glu Val Phe Asp Lys Phe Lys Ser Ser Lys Leu Tyr
        275                 280                 285

Tyr Phe Thr Asp Ile Val Ser Lys Gly Ser Ser Ile Ile Asn Val Glu
    290                 295                 300

Tyr Arg Arg Asp Leu Ala Asn Arg Leu Asp Trp Leu Gly Val Asn Tyr
305                 310                 315                 320

Tyr Ser Arg Leu Val Tyr Lys Ile Val Asp Asp Lys Pro Ile Ile Leu
                325                 330                 335

His Gly Tyr Gly Phe Leu Cys Thr Pro Gly Gly Ile Ser Pro Ala Glu
            340                 345                 350

Asn Pro Cys Ser Asp Phe Gly Trp Glu Val Tyr Pro Glu Gly Leu Tyr
        355                 360                 365
```

```
Leu Leu Leu Lys Glu Leu Tyr Asn Arg Tyr Gly Val Asp Leu Ile Val
    370                 375                 380

Thr Glu Asn Gly Val Ser Asp Ser Arg Asp Ala Leu Arg Pro Ala Tyr
385                 390                 395                 400

Leu Val Ser His Val Tyr Ser Val Trp Lys Ala Ala Asn Glu Gly Ile
                405                 410                 415

Pro Val Lys Gly Tyr Leu His Trp Ser Leu Thr Asp Asn Tyr Glu Trp
            420                 425                 430

Ala Gln Gly Phe Arg Gln Lys Phe Gly Leu Val Met Val Asp Phe Lys
        435                 440                 445

Thr Lys Lys Arg Tyr Leu Arg Pro Ser Ala Leu Val Phe Arg Glu Ile
    450                 455                 460

Ala Thr His Asn Gly Ile Pro Asp Glu Leu Gln His Leu Thr Leu Ile
465                 470                 475                 480

Gln


<210> SEQ ID NO 23
<211> LENGTH: 25
<212> TYPE: DNA
<213> ORGANISM: Artificial
<220> FEATURE:
<223> OTHER INFORMATION: primer

<400> SEQUENCE: 23

ttcgaggaaa tagccactca aaaag                                           25


<210> SEQ ID NO 24
<211> LENGTH: 24
<212> TYPE: DNA
<213> ORGANISM: Artificial
<220> FEATURE:
<223> OTHER INFORMATION: primer

<400> SEQUENCE: 24

taccagggcg cttggcctta aata                                            24


<210> SEQ ID NO 25
<211> LENGTH: 27
<212> TYPE: DNA
<213> ORGANISM: Artificial
<220> FEATURE:
<223> OTHER INFORMATION: primer

<400> SEQUENCE: 25

ttcggtgaaa tagccactca aaaagaa                                         27


<210> SEQ ID NO 26
<211> LENGTH: 24
<212> TYPE: DNA
<213> ORGANISM: Artificial
<220> FEATURE:
<223> OTHER INFORMATION: primer

<400> SEQUENCE: 26

taccagggcg cttggcctta aata                                            24


<210> SEQ ID NO 27
<211> LENGTH: 30
<212> TYPE: DNA
<213> ORGANISM: Artificial
<220> FEATURE:
<223> OTHER INFORMATION: primer
```

<400> SEQUENCE: 27
agaaggatag ccactcaaaa agaaattcca 30

<210> SEQ ID NO 28
<211> LENGTH: 24
<212> TYPE: DNA
<213> ORGANISM: Artificial
<220> FEATURE:
<223> OTHER INFORMATION: primer

<400> SEQUENCE: 28
taccagggcg cttggcctta aata 24

<210> SEQ ID NO 29
<211> LENGTH: 24
<212> TYPE: DNA
<213> ORGANISM: Artificial
<220> FEATURE:
<223> OTHER INFORMATION: primer

<400> SEQUENCE: 29
ggattagctc acctcgcaga cctc 24

<210> SEQ ID NO 30
<211> LENGTH: 26
<212> TYPE: DNA
<213> ORGANISM: Artificial
<220> FEATURE:
<223> OTHER INFORMATION: primer

<400> SEQUENCE: 30
aataccaggg cgcttggcct taaata 26

<210> SEQ ID NO 31
<211> LENGTH: 1416
<212> TYPE: DNA
<213> ORGANISM: Pyrococcus furiosus R170A/R220A/Y227F/R448E

<400> SEQUENCE: 31
gcaaagttcc caaaaaactt catgtttgga tattcttggt ctggtttcca gtttgagatg 60
ggactgccag gaagtgaagt ggaaagcgac tggtgggtgt gggttcacga caaggagaac 120
atagcatcag gtctagtaag tggagatcta ccagagaacg gcccagcata ttggcacctc 180
tataagcaag atcatgacat tgcagaaaag ctaggaatgg attgtattag aggtggcatt 240
gagtgggcaa gaatttttcc aaagccaaca tttgacgtta aagttgatgt ggaaaaggat 300
gaagaaggca acataatttc cgtagacgtt ccagagagta caataaaaga gctagagaaa 360
attgccaaca tggaggccct tgaacattat cgcaagattt actcagactg gaaggagagg 420
ggcaaaacct tcatattaaa cctctaccac tggcctcttc cattatggat tcatgaccca 480
attgcagtaa ggaaacttgg cccggatgcg gctcctgcag gatggttaga tgagaagaca 540
gtggtagagt ttgtgaagtt tgccgccttc gttgcttatc accttgatga cctcgttgac 600
atgtggagca caatgaacga accaaacgta gtctacaatc aaggttacat taatctagct 660
tcaggatttc caccaggatt tctaagcttt gaagcagcag aaaaggcaaa attcaactta 720
attcaggctc acatcggagc atatgatgcc ataaaagagt attcagaaaa atccgtggga 780
gtgatatacg cctttgcttg gcacgatcct ctagcggagg agtataagga tgaagtagag 840
gaaatcagaa agaaagacta tgagtttgta acaattctac actcaaaagg aaagctagac 900

```
tggatcggcg taaactacta ctccaggctg gtatatggag ccaaagatgg acacctagtt    960

cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cgaggaaata gccactcaaa aagaaattcc agaagaatta   1380

gctcacctcg cagacctcaa atttgttaca agaaag                             1416
```

```
<210> SEQ ID NO 32
<211> LENGTH: 1416
<212> TYPE: DNA
<213> ORGANISM: Pyrococcus furiosus R170/R220A/Y227F/R448G

<400> SEQUENCE: 32

gcaaagttcc caaaaaactt catgtttgga tattcttggt ctggtttcca gtttgagatg     60

ggactgccag gaagtgaagt ggaaagcgac tggtgggtgt gggttcacga caaggagaac    120

atagcatcag gtctagtaag tggagatcta ccagagaacg gcccagcata ttggcacctc    180

tataagcaag atcatgacat tgcagaaaag ctaggaatgg attgtattag aggtggcatt    240

gagtgggcaa gaatttttcc aaagccaaca tttgacgtta aagttgatgt ggaaaaggat    300

gaagaaggca acataatttc cgtagacgtt ccagagagta caataaaaga gctagagaaa    360

attgccaaca tggaggccct tgaacattat cgcaagattt actcagactg gaaggagagg    420

ggcaaaacct tcatattaaa cctctaccac tggcctcttc cattatggat tcatgaccca    480

attgcagtaa ggaaacttgg cccggatgcg gctcctgcag gatggttaga tgagaagaca    540

gtggtagagt ttgtgaagtt tgccgccttc gttgcttatc accttgatga cctcgttgac    600

atgtggagca caatgaacga accaaacgta gtctacaatc aaggttacat taatctagct    660

tcaggatttc caccaggatt tctaagcttt gaagcagcag aaaaggcaaa attcaactta    720

attcaggctc acatcggagc atatgatgcc ataaaagagt attcagaaaa atccgtggga    780

gtgatatacg cctttgcttg gcacgatcct ctagcggagg agtataagga tgaagtagag    840

gaaatcagaa agaaagacta tgagtttgta acaattctac actcaaaagg aaagctagac    900

tggatcggcg taaactacta ctccaggctg gtatatggag ccaaagatgg acacctagtt    960

cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cggtgaaata gccactcaaa aagaaattcc agaagaatta   1380

gctcacctcg cagacctcaa atttgttaca agaaag                             1416
```

```
<210> SEQ ID NO 33
<211> LENGTH: 1416
<212> TYPE: DNA
<213> ORGANISM: Pyrococcus furiosus R170/R220A/Y227F/E449R
```

<400> SEQUENCE: 33

```
gcaaagttcc caaaaaactt catgtttgga tattcttggt ctggtttcca gtttgagatg     60
ggactgccag gaagtgaagt ggaaagcgac tggtgggtgt gggttcacga caaggagaac    120
atagcatcag gtctagtaag tggagatcta ccagagaacg gcccagcata ttggcacctc    180
tataagcaag atcatgacat tgcagaaaag ctaggaatgg attgtattag aggtggcatt    240
gagtgggcaa gaatttttcc aaagccaaca tttgacgtta aagttgatgt ggaaaaggat    300
gaagaaggca acataatttc cgtagacgtt ccagagagta caataaaaga gctagagaaa    360
attgccaaca tggaggccct tgaacattat cgcaagattt actcagactg gaaggagagg    420
ggcaaaacct tcatattaaa cctctaccac tggcctcttc cattatggat tcatgaccca    480
attgcagtaa ggaaacttgg cccggatgcg gctcctgcag gatggttaga tgagaagaca    540
gtggtagagt ttgtgaagtt tgccgccttc gttgcttatc accttgatga cctcgttgac    600
atgtggagca caatgaacga accaaacgta gtctacaatc aaggttacat taatctagct    660
tcaggatttc caccaggatt tctaagcttt gaagcagcag aaaaggcaaa attcaactta    720
attcaggctc acatcggagc atatgatgcc ataaaagagt attcagaaaa atccgtggga    780
gtgatatacg cctttgcttg gcacgatcct ctagcggagg agtataagga tgaagtagag    840
gaaatcagaa agaaagacta tgagtttgta acaattctac actcaaaagg aaagctagac    900
tggatcggcg taaactacta ctccaggctg gtatatggag ccaaagatgg acacctagtt    960
cctttacctg gatatggatt tatgagtgag agaggaggat ttgcaaagtc aggaagacct   1020
gctagtgact ttggatggga aatgtaccca gagggccttg agaaccttct taagtattta   1080
aacaatgcct acgagctacc aatgataatt acagagaacg gtatggccga tgcagcagat   1140
agatacaggc cacactatct cgtaagccat ctaaaggcag tttacaatgc tatgaaagaa   1200
ggtgctgatg ttagagggta tctccactgg tctctaacag acaactacga atgggcccaa   1260
gggttcagga tgagatttgg attggtttac gtggatttcg agacaaagaa gagatattta   1320
aggccaagcg ccctggtatt cagaaggata gccactcaaa aagaaattcc agaagaatta   1380
gctcacctcg cagacctcaa atttgttaca agaaag                             1416
```

<210> SEQ ID NO 34
<211> LENGTH: 1416
<212> TYPE: DNA
<213> ORGANISM: Pyrococcus furiosus R170/R220A/Y227F/E459G

<400> SEQUENCE: 34

```
gcaaagttcc caaaaaactt catgtttgga tattcttggt ctggtttcca gtttgagatg     60
ggactgccag gaagtgaagt ggaaagcgac tggtgggtgt gggttcacga caaggagaac    120
atagcatcag gtctagtaag tggagatcta ccagagaacg gcccagcata ttggcacctc    180
tataagcaag atcatgacat tgcagaaaag ctaggaatgg attgtattag aggtggcatt    240
gagtgggcaa gaatttttcc aaagccaaca tttgacgtta aagttgatgt ggaaaaggat    300
gaagaaggca acataatttc cgtagacgtt ccagagagta caataaaaga gctagagaaa    360
attgccaaca tggaggccct tgaacattat cgcaagattt actcagactg gaaggagagg    420
ggcaaaacct tcatattaaa cctctaccac tggcctcttc cattatggat tcatgaccca    480
attgcagtaa ggaaacttgg cccggatgcg gctcctgcag gatggttaga tgagaagaca    540
gtggtagagt ttgtgaagtt tgccgccttc gttgcttatc accttgatga cctcgttgac    600
```

```
atgtggagca caatgaacga accaaacgta gtctacaatc aaggttacat taatctagct    660

tcaggatttc caccaggatt tctaagcttt gaagcagcag aaaaggcaaa attcaactta    720

attcaggctc acatcggagc atatgatgcc ataaaagagt attcagaaaa atccgtggga    780

gtgatatacg cctttgcttg gcacgatcct ctagcggagg agtataagga tgaagtagag    840

gaaatcagaa agaaagacta tgagtttgta acaattctac actcaaaagg aaagctagac    900

tggatcggcg taaactacta ctccaggctg gtatatggag ccaaagatgg acacctagtt    960

cctttacctg gatatggatt tatgagtgag agaggaggat ttgcaaagtc aggaagacct   1020

gctagtgact ttggatggga aatgtaccca gagggccttg agaaccttct taagtattta   1080

aacaatgcct acgagctacc aatgataatt acagagaacg gtatggccga tgcagcagat   1140

agatacaggc cacactatct cgtaagccat ctaaaggcag tttacaatgc tatgaaagaa   1200

ggtgctgatg ttagagggta tctccactgg tctctaacag acaactacga atgggcccaa   1260

gggttcagga tgagatttgg attggtttac gtggatttcg agacaaagaa gagatattta   1320

aggccaagcg ccctggtatt cagagaaata gccactcaaa aagaaattcc agaaggatta   1380

gctcacctcg cagacctcaa atttgttaca agaaag                             1416
```

```
<210> SEQ ID NO 35
<211> LENGTH: 472
<212> TYPE: PRT
<213> ORGANISM: Pyrococcus furiosus R170A/R220A/Y227F/R448E

<400> SEQUENCE: 35

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Phe Leu Ser Phe Glu Ala Ala Glu Lys Ala Lys Phe Asn Leu
```

```
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Glu
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 36
<211> LENGTH: 472
<212> TYPE: PRT
<213> ORGANISM: Pyrococcus furiosus R170A/R220A/Y227F/R448G

<400> SEQUENCE: 36

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125
```

```
His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Phe Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Gly
        435                 440                 445

Glu Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 37
<211> LENGTH: 472
<212> TYPE: PRT
<213> ORGANISM: Pyrococcus furiosus R170A/R220A/Y227F/E449R

<400> SEQUENCE: 37

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30
```

```
Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Phe Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350

Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445
```

```
Arg Ile Ala Thr Gln Lys Glu Ile Pro Glu Glu Leu Ala His Leu Ala
    450                 455                 460

Asp Leu Lys Phe Val Thr Arg Lys
465                 470


<210> SEQ ID NO 38
<211> LENGTH: 472
<212> TYPE: PRT
<213> ORGANISM: Pyrococcus furiosus R170A/R220A/Y227F/E459G

<400> SEQUENCE: 38

Ala Lys Phe Pro Lys Asn Phe Met Phe Gly Tyr Ser Trp Ser Gly Phe
1               5                   10                  15

Gln Phe Glu Met Gly Leu Pro Gly Ser Glu Val Glu Ser Asp Trp Trp
            20                  25                  30

Val Trp Val His Asp Lys Glu Asn Ile Ala Ser Gly Leu Val Ser Gly
        35                  40                  45

Asp Leu Pro Glu Asn Gly Pro Ala Tyr Trp His Leu Tyr Lys Gln Asp
    50                  55                  60

His Asp Ile Ala Glu Lys Leu Gly Met Asp Cys Ile Arg Gly Gly Ile
65                  70                  75                  80

Glu Trp Ala Arg Ile Phe Pro Lys Pro Thr Phe Asp Val Lys Val Asp
                85                  90                  95

Val Glu Lys Asp Glu Glu Gly Asn Ile Ile Ser Val Asp Val Pro Glu
            100                 105                 110

Ser Thr Ile Lys Glu Leu Glu Lys Ile Ala Asn Met Glu Ala Leu Glu
        115                 120                 125

His Tyr Arg Lys Ile Tyr Ser Asp Trp Lys Glu Arg Gly Lys Thr Phe
    130                 135                 140

Ile Leu Asn Leu Tyr His Trp Pro Leu Pro Leu Trp Ile His Asp Pro
145                 150                 155                 160

Ile Ala Val Arg Lys Leu Gly Pro Asp Ala Ala Pro Ala Gly Trp Leu
                165                 170                 175

Asp Glu Lys Thr Val Val Glu Phe Val Lys Phe Ala Ala Phe Val Ala
            180                 185                 190

Tyr His Leu Asp Asp Leu Val Asp Met Trp Ser Thr Met Asn Glu Pro
        195                 200                 205

Asn Val Val Tyr Asn Gln Gly Tyr Ile Asn Leu Ala Ser Gly Phe Pro
    210                 215                 220

Pro Gly Phe Leu Ser Phe Glu Ala Ala Glu Lys Ala Lys Phe Asn Leu
225                 230                 235                 240

Ile Gln Ala His Ile Gly Ala Tyr Asp Ala Ile Lys Glu Tyr Ser Glu
                245                 250                 255

Lys Ser Val Gly Val Ile Tyr Ala Phe Ala Trp His Asp Pro Leu Ala
            260                 265                 270

Glu Glu Tyr Lys Asp Glu Val Glu Glu Ile Arg Lys Lys Asp Tyr Glu
        275                 280                 285

Phe Val Thr Ile Leu His Ser Lys Gly Lys Leu Asp Trp Ile Gly Val
    290                 295                 300

Asn Tyr Tyr Ser Arg Leu Val Tyr Gly Ala Lys Asp Gly His Leu Val
305                 310                 315                 320

Pro Leu Pro Gly Tyr Gly Phe Met Ser Glu Arg Gly Gly Phe Ala Lys
                325                 330                 335

Ser Gly Arg Pro Ala Ser Asp Phe Gly Trp Glu Met Tyr Pro Glu Gly
            340                 345                 350
```

-continued

```
Leu Glu Asn Leu Leu Lys Tyr Leu Asn Asn Ala Tyr Glu Leu Pro Met
        355                 360                 365

Ile Ile Thr Glu Asn Gly Met Ala Asp Ala Ala Asp Arg Tyr Arg Pro
    370                 375                 380

His Tyr Leu Val Ser His Leu Lys Ala Val Tyr Asn Ala Met Lys Glu
385                 390                 395                 400

Gly Ala Asp Val Arg Gly Tyr Leu His Trp Ser Leu Thr Asp Asn Tyr
                405                 410                 415

Glu Trp Ala Gln Gly Phe Arg Met Arg Phe Gly Leu Val Tyr Val Asp
            420                 425                 430

Phe Glu Thr Lys Lys Arg Tyr Leu Arg Pro Ser Ala Leu Val Phe Arg
        435                 440                 445

Glu Ile Ala Thr Gln Lys Glu Ile Pro Glu Gly Leu Ala His Leu Ala
    450                 455                 460

Asp Leu Lys Phe Val Thr Arg Lys
465                 470
```

MUTANT β-GLUCOSIDASE, ENZYME COMPOSITION FOR DECOMPOSING BIOMASS, AND METHOD OF PRODUCING SUGAR SOLUTION

TECHNICAL FIELD

This disclosure relates to a novel β-glucosidase, an enzyme composition that decomposes biomass comprising the β-glucosidase, and methods of producing sugar solutions by hydrolysis of cellulose-derived biomass with the β-glucosidase.

BACKGROUND

Cellulose can be saccharified by various methods. Among them, enzymatic saccharification, which has low energy consumption and a high sugar yield, has been chiefly developed. Cellulase, a cellulolytic enzyme, is roughly classified into cellobiohydrolase, which acts on the crystalline region of cellulose, and endoglucanase, which acts internally on cellulose molecular chain to reduce the molecular weight. These cellulases are known to be inhibited by one of their products, cellobiose. Beta-glucosidase is an enzyme that acts on water-soluble oligosaccharide or cellobiose and catalyzes hydrolysis of the β-glycosidic bond. In particular, β-glucosidases are essential enzymes to sufficiently obtain glucose, which is a useful fermentation raw material. It is known that the reaction of cellobiohydrolase and endoglucanase is inhibited by accumulation of cellobiose generated by cellulose decomposition. That is, the β-glucosidase can significantly reduce accumulation of cellobiose generated by cellulose decomposition and thereby has an effect of notably improving cellulose decomposition efficiency.

Cellulose is contained in herbaceous plants and arboreous plants in large amounts. These plants are collectively called "cellulose-containing biomass." The cellulose-containing biomass contains hemicellulose such as xylan and arabinan, and lignin, in addition to cellulose. In particular, the lignin contained in cellulose-containing biomass is an aromatic polymer compound and is known to have inhibitory activity on enzymatic saccharification using filamentous fungal-derived cellulase. Though the inhibitory mechanism of lignin on the filamentous fungal-derived cellulase has not completely been elucidated, adsorption of cellulase to lignin is believed as one of factors of reducing the decomposition efficiency (P. Hetti et al., Journal of Biotechnology, 107, 65-72 (2004)).

Thermostable enzymes have high stability and retain activity for a long time even under high temperature conditions, and the use thereof as industrial enzymes has been investigated. Such thermostable enzymes have been confirmed to be highly present as enzymes possessed by thermophilic bacteria or hyperthermophilic bacteria.

Thermostable β-glucosidases also have been identified from several thermophilic bacteria or hyperthermophilic bacteria. Specifically, thermostable β-glucosidases have been identified from microorganisms such as *Pyrococcus furiosus, Pyrococcus horikoshii, Thermotoga maritima, Sulfolobus shibatae, Sulfolobus solfataricus*, and *Clostridium thermocellum*. In particular, it is disclosed that the β-glucosidase derived from *Clostridium thermocellum* forms a monomer (P. Christian et al., *Trichoderma* and *Gliocladium*: Basic Biology, Taxonomy and Genetics., Vol. 1, 121-138 (1998)) and that the β-glucosidase derived from *Sulfolobus solfataricus* or *Pyrococcus furiosus* forms a tetramer (H. Ohba et al., Biosci. Biotech. Biochem., 59, 1581-1583 (1995) and MW Bauer et al., J. Biol. Chem., Vol. 271, 39, 23749-23755 (1996)). The relationship between these structures and their functions has not yet been revealed.

It could therefore be helpful to provide a β-glucosidase having high enzyme activity of hydrolyzing cellulose-containing biomass.

SUMMARY

We introduced amino acid mutation into specific sites in a conventional β-glucosidase having the amino acid sequence shown in SEQ ID NO: 1 (hereinafter, referred to as "parent β-glucosidase") and succeeded in acquiring a novel β-glucosidase as a mutant having improved functional properties. More specifically, we focused on the three-dimensional structure of the parent β-glucosidase, specified amino acids involved in formation of a tetramer thereof by protein crystal structure analysis, and selectively mutated the amino acids to successfully obtain a novel β-glucosidase of which tetramer formation is unstable. We found that this novel β-glucosidase has excellent characteristics in, in particular, hydrolysis of cellulose-containing biomass.

We thus provide:

[1] A mutant β-glucosidase comprising a mutation at a position of amino acid that forms a hydrogen bond or an ionic bond between monomers, wherein the mutation makes tetramer formation of the β-glucosidase unstable, and having a cellobiose decomposition activity equivalent to or higher than that of a wild-type;

[2] The mutant β-glucosidase according to [1], comprising an amino acid sequence having a sequence homology of at least 90% to the amino acid sequence of SEQ ID NO: 1, wherein the amino acid sequence having a sequence homology of at least 90% comprises mutations of amino acids corresponding to at least three amino acids selected from the group consisting of glutamic acid at position 39, aspartic acid at position 169, arginine at position 170, arginine at position 220, tyrosine at position 227, and glutamic acid at position 330 in the amino acid sequence of SEQ ID NO: 1;

[3] The mutant β-glucosidase according to [1] or [2], comprising an amino acid sequence having a sequence homology of at least 90% to the amino acid sequence of SEQ ID NO: 1, wherein the amino acid sequence having a sequence homology of at least 90% comprises substitutions of amino acids corresponding to at least three amino acids selected from the group consisting of glutamic acid at position 39, aspartic acid at position 169, arginine at position 170, arginine at position 220, tyrosine at position 227, and glutamic acid at position 330 in the amino acid sequence of SEQ ID NO: 1 with amino acids having neutral side chains;

[4] The mutant β-glucosidase according to any one of [1] to [3], comprising an amino acid sequence having a sequence homology of at least 90% to the amino acid sequence of SEQ ID NO: 1, wherein the amino acid sequence having a sequence homology of at least 90% comprises substitutions of amino acids corresponding to arginine at position 170, arginine at position 220, and tyrosine at position 227 in the amino acid sequence of SEQ ID NO: 1 with amino acids having neutral side chains;

[5] The mutant β-glucosidase according to [3] or [4], wherein the amino acids having neutral side chains are selected from the group consisting of alanine, phenylalanine, and glycine;

[6] The mutant β-glucosidase according to any one of [1] to [5], comprising an amino acid sequence having a sequence homology of at least 90% to the amino acid sequence of SEQ ID NO: 1, wherein the amino acid sequence having a sequence homology of at least 90% comprises a substitution of an amino acid corresponding to arginine at position 170 in the amino acid sequence of SEQ ID NO: 1 with alanine; a substitution of an amino acid corresponding to arginine at position 220 in the amino acid sequence of SEQ ID NO: 1 with alanine; and a substitution of an amino acid corresponding to tyrosine at position 227 in the amino acid sequence of SEQ ID NO: 1 with phenylalanine;

[7] The mutant β-glucosidase according to any one of [1] to [6], comprising the amino acid sequence shown in SEQ ID NO: 14;

[8] The mutant β-glucosidase according to any one of [1] to [7], further comprising a mutation of an amino acid corresponding to at least one amino acid selected from the group consisting of leucine at position 440, arginine at position 448, glutamic acid at position 449, and glutamic acid at position 459 in the amino acid sequence of SEQ ID NO: 1;

[9] The mutant β-glucosidase according to [8], comprising at least one substitution selected from the group consisting of a substitution of an amino acid corresponding to arginine at position 448 in the amino acid sequence of SEQ ID NO: 1 with an amino acid having a neutral side chain or an acidic side chain; a substitution of an amino acid corresponding to glutamic acid at position 449 in the amino acid sequence of SEQ ID NO: 1 with an amino acid having a neutral side chain or a basic side chain; and a substitution of an amino acid corresponding to glutamic acid at position 459 in the amino acid sequence of SEQ ID NO: 1 with an amino acid having a neutral side chain or a basic side chain;

[10] The mutant β-glucosidase according to [8] or [9], comprising an amino acid sequence shown in any one of SEQ ID NOs: 35 to 38;

[11] A DNA encoding the mutant β-glucosidase according to any one of [1] to [10];

[12] The DNA according to [11], comprising a nucleotide sequence shown in any one of SEQ ID NO: 20 and SEQ ID NOs: 31 to 34;

[13] An expression vector comprising the DNA according to [11] or [12];

[14] A transformed cell produced by transformation using the expression vector according to [13];

[15] An enzyme composition for decomposing biomass, comprising the mutant β-glucosidase according to any one of [1] to [10] or a processed product of the transformed cell according to [14]; and

[16] A method of producing a sugar solution from cellulose-derived biomass, the method comprising hydrolyzing cellulose-containing biomass with the biomass-decomposing enzyme composition according to [15].

This application claims priority to Japanese Patent Application No. 2011-155792, the disclosure of which, including the specification and/or the drawings, is incorporated herein by reference in its entirety.

We provide a novel mutant β-glucosidase exhibiting improved glucosidase enzyme activity in the presence of cellulose-containing biomass. The β-glucosidase can be suitably used in production of a sugar solution by hydrolysis of cellulose-containing biomass.

DETAILED DESCRIPTION

Figure 1:
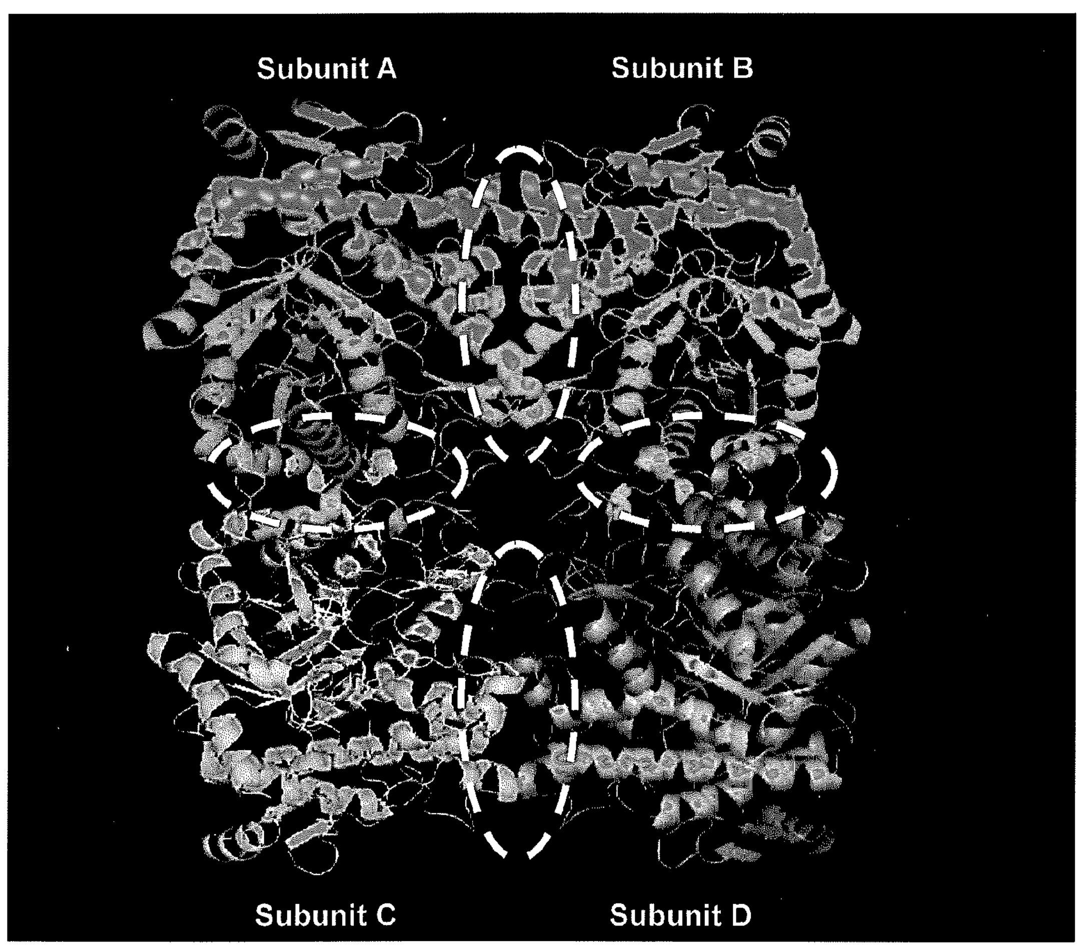
FIG. 1 is a ribbon model of the parent β-glucosidase, obtained from the results of crystal structure analysis of the parent β-glucosidase.

Our mutant β-glucosidases, compositions and methods will now be described in detail, but this disclosure is not limited thereto.

(1) β-glucosidase

The term "β-glucosidase" refers to an enzyme catalyzing hydrolysis of β-glucoside bond of sugar. The β-glucosidase characteristically has high activity of decomposing cellobiose. The cellobiose decomposition activity can be measured by, for example, adding an enzyme solution to a substrate solution of cellobiose dissolved in 50 mM acetic acid-sodium acetate buffer (pH 5.0), reacting them at 30° C. to 85° C. for 30 minutes, stopping the reaction optionally by, for example, changing the pH, and then quantifying the glucose level in the reaction solution with a glucose quantitative kit. Enzymes belonging to EC number: EC 3.2.1.21 are exemplified as β-glucosidase. However, those having the above-described cellobiose decomposition activity are included in the "β-glucosidase."

(2) Parent β-glucosidase

The parent β-glucosidase is a β-glucosidase comprising the amino acid sequence shown in SEQ ID NO: 1 and has a cellobiose decomposition activity. The term "parent β-glucosidase" is also mentioned as "wild-type." In this case, the term "parent β-glucosidase" and the term "wild-type" are interchangeably used.

The parent β-glucosidase is an enzyme derived from *Pyrococcus furiosus*. *Pyrococcus furiosus* is a microorganism classified in archaebacterium having a growth optimum temperature of 80° C. to 110° C. and can assimilate various carbon sources such as starch, cellulose, maltose, and pullulan.

The parent β-glucosidase is an enzyme isolated and purified for the first time by Kengen, et al. (Eur. J. Biochem., 213, 305-312, 1993). It is clearly described in Kengen that the parent β-glucosidase is present in a homotetrameric form having a molecular weight of about 230 kDa in an aqueous solution. It is also described that the tetramer can be destroyed with a surfactant such as SDS and that each monomer has a molecular weight of about 58 kDa. Furthermore, it is described that the parent β-glucosidase has an optimum pH of 5.0, an isoelectric point of 4.4, and a reaction optimum temperature of 102° C. to 105° C. The amino acid sequence of the parent β-glucosidase shown in SEQ ID NO: 1 is based on that identified by Voorhorst, et al. (J. Bacteriol., 177, 24, 7105-7111, 1995). It is described that the molecular weight based on this amino acid sequence is about 54 kDa (54.58 kDa).

(3) Our Mutant β-glucosidase

Our mutant β-glucosidase comprises a mutation at a position of an amino acid that forms a hydrogen bond or ionic bond between β-glucosidase monomers in an aqueous solution, wherein the mutation makes the tetramer formation of the β-glucosidase unstable.

Our mutant β-glucosidase is present in a tetrameric form that is unstable compared to the tetramer originally formed by the parent β-glucosidase in an aqueous solution. It is known that the parent β-glucosidase in the primary structure has a molecular weight of about 54 kDa and forms a stable tetramer that is dissolved in an aqueous solution as a molecule having a molecular weight of 200 kDa or more (Bauer MW., et al., "Comparison of a β-glucosidase and a β-mannosidase from the hyperthermophilic archaeon *Pyrococcus furiosus*," J. Biol. Chem., vol. 271, 39, 23749-23755 (1996)).

Formation of an unstable tetramer of our mutant β-glucosidase in an aqueous solution can be confirmed by the molecular weight in the aqueous solution being less than 200 kDa; specifically, the molecular weight detected by Native-PAGE being less than 160 kDa. The tetramer being unstable in an aqueous solution can also be confirmed by comparing the behavior of the parent β-glucosidase and our mutant β-glucosidase in an aqueous solution by a method other than Native-PAGE (for example, gel filtration or ultracentrifugation). Specifically, the tetramer being unstable can be confirmed by the molecular weight of our β-glucosidase being smaller than that of the parent β-glucosidase in an aqueous solution.

As described in detail in the examples below, we demonstrated by crystal structure analysis that in the amino acid sequence of the parent β-glucosidase, i.e., in the amino acid sequence shown in SEQ ID NO: 1, glutamic acid at position 39 (hereinafter referred to as "Glu39"), aspartic acid at position 169 (hereinafter referred to as "Asp169"), arginine at position 170 (hereinafter referred to as "Arg170"), arginine at position 220 (hereinafter referred to as "Arg220"), tyrosine at position 227 (hereinafter referred to as "Try227"), and glutamic acid at position 330 (hereinafter referred to as "Glu330") are involved in formation of a tetramer of the parent β-glucosidase in an aqueous solution. That is, we found that these amino acids form a hydrogen bond or ionic bond with another monomer of the parent glucosidase in an aqueous solution and are highly involved in formation of a tetramer. The purpose of introducing an amino acid mutation into a β-glucosidase is to destroy the hydrogen bond or the ionic bond of the amino acid involved in the formation of a tetramer and, as a result, to make the tetramer structure of the β-glucosidase unstable in an aqueous solution.

The amino acid mutation of our β-glucosidase includes a substitution and/or a deletion of an amino acid involved in the formation of a tetramer of the β-glucosidase in an aqueous solution.

Our mutant β-glucosidase preferably includes an amino acid sequence having a sequence homology of 90%, 95%, or 99% or more to the amino acid sequence of SEQ ID NO: 1. The amino acid sequence having such a sequence homology includes substitutions of amino acids corresponding to at least three amino acids selected from Glu39, Asp169, Arg170, Arg220, Tyr227, and Glu330 in the amino acid sequence of SEQ ID NO: 1 with amino acids having neutral side chains.

The "amino acid sequence having a sequence homology of 90%, 95%, or 99% or more to the amino acid sequence of SEQ ID NO: 1" at least retains the activity of the β-glucosidase represented by the amino acid sequence of SEQ ID NO: 1.

The "amino acids corresponding to amino acids in the amino acid sequence of SEQ ID NO: 1" means that the amino acids in the amino acid sequence having the above-mentioned sequence homology are present at the same positions as Glu39, Asp169, Arg170, Arg220, Tyr227, and Glu330 in the amino acid sequence of SEQ ID NO: 1 in comparison of the conformations of the amino acid sequence having the above-mentioned sequence homology and the amino acid sequence of SEQ ID NO: 1 and that the amino acids are involved in tetramer formation of the β-glucosidase in an aqueous solution. The types of the "amino acids" are respectively the same as Glu39, Asp169, Arg170, Arg220, Tyr227, and Glu330 in the amino acid sequence of SEQ ID NO: 1.

More preferably, our mutant β-glucosidase includes an amino acid sequence having a sequence homology of 90%, 95%, or 99% or more to the amino acid sequence of SEQ ID NO: 1, and the amino acid sequence having such a sequence homology includes substitutions of amino acids corresponding to Arg170, Arg220, and Tyr227 in the amino acid sequence of SEQ ID NO: 1 with amino acids having neutral side chains.

Examples of the "amino acids having neutral side chains" include glycine, asparagine, glutamine, serine, threonine, tyrosine, cysteine, alanine, valine, leucine, isoleucine, proline, phenylalanine, methionine, and tryptophan. The "amino acids having neutral side chains" are preferably selected from the group consisting of alanine, phenylalanine, and glycine.

As described in detail in the examples below, we demonstrated by crystal structure analysis that in the parent β-glucosidase, Arg170 in the amino acid sequence shown in SEQ ID NO: 1 forms a hydrogen bond or an ionic bond with Arg170 of other all parent glucosidase monomers that form a tetramer in an aqueous solution. That is, the hydrogen bond or the ionic bond participating in tetramer formation can be effectively destroyed by introducing mutation to Arg170. As described in detail in the examples below, we demonstrated by crystal structure analysis that in the parent β-glucosidase, Arg220 forms a hydrogen bond with glycine at position 44 (Gly44) in another monomer forming the tetramer and that Tyr227 forms a hydrogen bond with lysine at position 165 (Lys165) in another monomer forming the tetramer in an aqueous solution. That is, it is possible to effectively destroy the hydrogen bond or ionic bond participating in tetramer formation by introducing mutation into Arg220 and Tyr227, in addition to Arg170, in the amino acid sequence shown in SEQ ID NO: 1 and thereby to make a tetramer structure of β-glucosidases unstable in an aqueous solution.

Accordingly, preferably, our mutant β-glucosidase includes an amino acid sequence having a sequence homology of 90%, 95%, or 99% or more to the amino acid sequence of SEQ ID NO: 1, and the amino acid sequence having such a sequence homology includes substitutions of amino acids corresponding to Arg170, Arg220, and Tyr227 of the amino acid sequence of SEQ ID NO: 1 with alanine, alanine, and phenylalanine, respectively.

Particularly preferably, our mutant β-glucosidase includes the amino acid sequence shown in SEQ ID NO: 14.

As long as the cellobiose decomposition activity is retained, our mutant β-glucosidase may include an amino acid sequence having a sequence homology of 90%, 95%, or 99% or more to the amino acid sequence of SEQ ID NO: 1, and the amino acid sequence having such a sequence homology may include mutation of one or multiple amino acids at sites other than the amino acids corresponding to Glu39, Asp169, Arg170, Arg220, Tyr227, and Glu330 of the amino acid sequence of SEQ ID NO: 1. The term "multiple" means 2 to 10, preferably 2 to 5, and more preferably 2 to 3, and the term "mutation of amino acid(s)" includes substitution, deletion, insertion, and/or addition of the amino acid(s).

Our mutant β-glucosidase has improved excellent properties such as an enhanced β-glucosidase activity in the presence of cellulose-containing biomass, compared to the parent β-glucosidase. The improved excellent properties are believed to be caused by that the tetramer structure of our mutant β-glucosidase is unstable due to the introduction of the above-described mutation, whereas the parent β-glucosidase forms a stable tetramer in an aqueous solution.

Our mutant β-glucosidase may be referred to as "mutant." In this case, the term "mutant β-glucosidase" and the term "mutant" are interchangeably used.

As described above, our mutant β-glucosidase includes an amino acid sequence having a sequence homology of 90%, 95%, or 99% or more to the amino acid sequence of SEQ ID NO: 1, and the amino acid sequence having such a sequence homology includes substitutions of at least three amino acids corresponding to amino acids selected from Glu39, Asp169, Arg170, Arg220, Tyr227, and Glu330 in the amino acid sequence of SEQ ID NO: 1 with amino acids having neutral side chains. As an effect of such mutation, the tetramer can be unstable. These mutants may be further introduced with mutation. The purpose of introduction of mutation is, for example, an enhancement in activity, an enhancement in thermal stability, and a decrease in stability of the multimer structure.

As described in detail in the examples below, we further performed crystal structure analysis of the above-described mutant β-glucosidase and, as a result, have revealed that our mutant β-glucosidase forms a dimer structure. The amino acids involved in the formation of the dimer structure of the mutant β-glucosidase are four amino acids corresponding to leucine at position 440, arginine at position 448, glutamic acid at position 449, and arginine at position 459 in the amino acid sequence of SEQ ID NO: 1. That is, these four amino acids form hydrogen bonds or ionic bonds with amino acids of the other mutant glucosidase forming the dimer and are highly involved in formation of the dimer of the mutant glucosidase. In addition to the above-described mutation that makes the tetramer unstable, mutation that makes the dimer formed by the mutant glucosidase unstable may further be introduced.

That is, our mutant β-glucosidase further includes mutation of amino acid corresponding to at least one amino acid selected from the group consisting of leucine at position 440, arginine at position 448, glutamic acid at position 449, and glutamic acid at position 459 in the amino acid sequence of SEQ ID NO: 1, in addition to the above-described mutation for making the tetramer unstable.

The "amino acid corresponding to amino acid in the amino acid sequence of SEQ ID NO: 1" means that the amino acid in the amino acid sequence having the above-mentioned sequence homology is present at the same position as leucine at position 440, arginine at position 448, glutamic acid at position 449, or glutamic acid at position 459 in the amino acid sequence of SEQ ID NO: 1 in comparison of conformations of the amino acid sequence having the above-mentioned sequence homology and the amino acid sequence of SEQ ID NO: 1 and that the amino acid is involved in dimer formation of the mutant β-glucosidase.

Particularly preferably, the above-described amino acid sequence of the mutant β-glucosidase includes a substitution of at least one amino acid position selected from the group consisting of a substitution of an amino acid corresponding to arginine at position 448 in the amino acid sequence of SEQ ID NO: 1 with an amino acid having a neutral or acidic side chain, a substitution of an amino acid corresponding to glutamic acid at position 449 with an amino acid having a neutral or basic side chain, and a substitution of an amino acid corresponding to arginine at position 459 with an amino acid having a neutral or basic side chain.

Examples of the "amino acid having a neutral side chain" include glycine, asparagine, glutamine, serine, threonine, tyrosine, cysteine, alanine, valine, leucine, isoleucine, proline, phenylalanine, methionine, and tryptophan. The "amino acid having a neutral side chain" is preferably selected from the group consisting of alanine, phenylalanine, and glycine.

The "amino acid having an acidic side chain" is selected from the group consisting of glutamic acid and aspartic acid.

The "amino acid having a basic side chain" is selected from the group consisting of arginine, lysine, and histidine.

Most preferably, the above-described amino acid sequence of the mutant β-glucosidase includes at least one mutation selected from a mutation of an amino acid corresponding to arginine at position 448 in the amino acid sequence of SEQ ID NO: 1 with glutamic acid or glycine, a mutation of an amino acid corresponding to glutamic acid at position 449 in the amino acid sequence of SEQ ID NO: 1 with arginine, and a mutation of an amino acid corresponding to arginine at position 459 in the amino acid sequence of SEQ ID NO: 1 with glycine.

Particularly preferably, our mutant β-glucosidase includes any of amino acid sequences shown in SEQ ID NOs: 31 to 34.

In addition such substitutions of amino acids, the mutant β-glucosidase may have deletion (elimination) of a region corresponding to all amino acids downstream from the position 440 in the amino acid sequence of SEQ ID NO: 1, a region corresponding to all amino acids downstream from the position 448 in the amino acid sequence of SEQ ID NO: 1, a region corresponding to all amino acids downstream from the position 449 in the amino acid sequence of SEQ ID NO: 1, or a region corresponding to all amino acids downstream from the position 459 in the amino acid sequence of SEQ ID NO: 1. This is because the sequence corresponding to the amino acids downstream from the position 440 does not particularly affect the cellobiose decomposition activity itself. Such deletion (elimination) can be achieved by inserting a stop codon into the gene at the site corresponding to the amino acids to be deleted.

(4) Method of Producing Our Mutant β-glucosidase

The mutant β-glucosidase can be produced by, for example, preparing a DNA encoding the amino acid sequence of β-glucosidase, ligating the DNA into an expression vector, introducing the expression vector into a host, and producing, isolating, and purifying the mutant β-glucosidase as a heterologous protein.

The DNA can be prepared by, for example, entirely synthesizing a DNA encoding an intended amino acid sequence by gene synthesis or introducing mutation into a DNA encoding an amino acid sequence having a sequence homology of 90%, 95%, or 99% or more to the amino acid sequence of SEQ ID NO: 1 at the above-mentioned predetermined positions by site-directed mutagenesis. The gene encoding an amino acid sequence having a sequence homology of 90%, 95%, or 99% or more to the amino acid sequence of SEQ ID NO: 1 can be obtained by isolating the DNA from a microorganism carrying the β-glucosidase, in particular, from *Pyrococcus furiosus* in accordance with a known method and amplifying the DNA by a method such as PCR.

The thus-prepared DNA encoding a mutant β-glucosidase is ligated to the downstream of a promoter in an appropriate expression vector using a restriction enzyme and a DNA ligase to produce an expression vector carrying the DNA.

Examples of the expression vector include bacterial plasmids; yeast plasmids; phage DNA (such as lambda phage); virus DNAs such as retroviruses, baculoviruses, vaccinia viruses, and adenoviruses; derivatives of SV40; and *agrobacteria* as vectors for plant cells. However, any other vector may be used as long as it is replicable and viable in the host cell. For example, when the host is *Escherichia coli*, for example, pUC, pET, or pBAD can be used. When the host is yeast, for example, pPink-HC, pPink-LC, pPinkα-HC, pPCIZ, pPCIZα, pPCI6, pPCI6α, pFLD1, pFLD1α, pGAPZ, pGAPZα, pPIC9K, or pPIC9 can be used.

The promoter may be any one that is suitable for the host cell used in expression of a gene. The promoter in the case using *Escherichia coli* as the host is, for example, a lac promoter, a Trp promoter, a PL promoter, or a PR promoter. The promoter in the case using yeast as the host is, for example, an AOX1 promoter, a TEF1 promoter, an ADE2 promoter, a CYC1 promoter, or a GAL-L1 promoter.

Preferred examples of the host cell include *Escherichia coli*, bacterial cells, yeast cells, filamentous fungal cells, insect cells, plant cells, and animal cells. Examples of the yeast cells include *Pichia, Saccharomyces*, and *Schizosaccharomyces*. Examples of the filamentous fungal cells include *Aspergillus* and *Trichoderma*. Examples of the insect cells include Sf9. Examples of the plant cells include dicotyledons. Examples of the animal cells include CHO, HeLa, and HEK293.

Transformation or transfection can be performed by a known method such as calcium phosphate transfection or electroporation. Our β-glucosidase can be obtained by expression in the thus-transformed or transfected host cells under control of a promoter and collection of the product. In the expression, after proliferation or growth of the host cells up to an appropriate cell density, the promoter is induced by chemical induction means such as temperature shift or addition of isopropyl-1-thio-β-D-galactoside (IPTG), and the cells are further cultured for a predetermined period of time.

When mutant β-glucosidase is extracellularly excreted, the β-glucosidase is purified directly from the culture medium. When mutant β-glucosidase is extracellularly located, the cells are destroyed by a physical means such as ultrasonic disintegration or mechanical disintegration or by a chemical means such as a cytolytic agent, and then β-glucosidase is purified. The β-glucosidase can be partially or completely purified from the culture medium of recombinant cells by combining technologies such as ammonium sulfate or ethanol precipitation, acid extraction, anion or cation exchange chromatography, reversed-phase high-performance liquid chromatography, affinity chromatography, gel filtration chromatography, and electrophoresis.

(5) Enzyme Composition for Decomposing Biomass, Containing Mutant β-glucosidase

Our mutant β-glucosidase has high thermal stability and lignin resistance in hydrolysis of cellulose-containing biomass, compared to parent β-glucosidase. Specifically, it is possible to obtain a cellobiose decomposition activity 1.2 times, 1.3 times, 1.4 times, 1.5 times, 1.6 times, 1.7 times, 1.8 times, 1.9 times, or 2 times or more than that of the parent β-glucosidase.

The mutant β-glucosidase may be purified or roughly purified one.

Our mutant β-glucosidase may be immobilized to a solid phase. Examples of the solid phase include polyacrylamide gel, polystyrene resins, porous glass, and metal oxides (but not limited thereto). The mutant β-glucosidase immobilized to a solid phase can be used continuously, repeatedly and is therefore advantageous.

Furthermore, a processed product of the cells transformed with a DNA encoding the mutant β-glucosidase can also be used as roughly purified mutant β-glucosidase. Examples of the "processed product of transformed cells" include transformed cells immobilized to a solid phase, killed bacteria or homogenate of transformed cells, and the killed bacteria or homogenate immobilized to a solid phase.

Our mutant β-glucosidase mixed with cellulase can be used as an enzyme composition for decomposing biomass to hydrolyze cellulose-containing biomass. The cellulase herein is not particularly limited as long as it has an activity of decomposing cellulose and may be a mixture. Examples of such enzymes include cellulases, hemicellulases, cellobiohydrolases, endoglucanases, exoglucanases, xylanases, and mannanases.

The cellulase is preferably a filamentous fungal-derived cellulase. The filamentous fungal-derived cellulase is a mixture at least containing both an endoglucanase and a cellobiohydrolase. A preferred filamentous fungal-derived cellulase for further efficiently saccharifying cellulose contains two or more endoglucanases and/or two or more cellobiohydrolases. Examples of microorganisms producing the filamentous fungal cellulase include *Trichoderma, Aspergillus, Cellulomonas, Clostridium, Streptomyces, Humicola, Acremonium, Irpex, Mucor*, and *Talaromyces*. These microorganisms produce cellulase in the culture medium. Accordingly, the culture medium may be directly used as raw filamentous fungal cellulase or may be used as a filamentous fungal cellulase mixture after purification and formulation. The filamentous fungal cellulase mixture purified from the culture medium and formulated may be used as a cellulase preparation further containing materials other than enzymes such as a protease inhibitor, a dispersant, a dissolution accelerator, and a stabilizer.

The filamentous fungal-derived cellulase is preferably a cellulase derived from *Trichoderma. Trichoderma* produces cellulase containing at least two endoglucanases and at least two cellobiohydrolases in the culture medium. The cellulase mixture prepared from such a culture medium can be preferably used. More preferably, the *Trichoderma* is *Trichoderma reesei*, and examples of cellulase mixtures derived from *Trichoderma reesei* include those derived from *Trichoderma reesei* QM9414, *Trichoderma reesei* QM9123, *Trichoderma reesei* Rut-30, *Trichoderma reesei* PC3-7, *Trichoderma reesei* CL-847, *Trichoderma reesei* MCG77, *Trichoderma reesei* MCG80, and *Trichoderma viride* QM9123. Furthermore, the *Trichoderma* may be a mutant strain of *Trichoderma* improved in cellulase productivity by mutagenesis treatment with, for example, a mutagen or ultraviolet irradiation.

The enzyme composition for decomposing biomass can be widely used in hydrolysis of cellulose-containing biomass. The cellulose-containing biomass is not limited as long as it contains at least cellulose. Specific examples thereof include bagasse, corn stover, corn cob, switchgrass, rice straw, wheat straw, trees, lumber, waste building materials, newspaper, used paper, and pulp. Such cellulose-containing biomass contains impurities such as aromatic polymer compounds, e.g., lignin and hemicellulose, and cellulose-containing biomass pretreated with, for example, an acid, an alkali, or pressurized/heated water to partially decompose lignin or hemicellulose may be used as cellulose.

The enzymatic treatment of our cellulose-containing biomass is preferably performed at a treatment temperature of 40° C. to 60° C., a treatment pH of 3 to 7, and a cellulose-containing biomass solid concentration of 0.1% to 30%. The decomposition efficiency of the enzyme composition for decomposing our biomass can be maximized within these ranges. Some of conventional glucosidases derived from thermophilic bacteria have an optimum reaction temperature of about 100° C. The glucosidase derived from thermophilic bacteria, however, exhibits a sufficiently high specific activity even at a temperature of 40° C. to 60° C. and can efficiently decompose cellulose-containing biomass in the presence of cellulase. This enzymatic treatment may be performed by a batch system or a continuous system. The hydrolysate obtained by such enzymatic treatment contains monosaccharide components such as glucose and xylose and can therefore be used as raw sugar for ethanol, lactic acid and the like.

EXAMPLES

Our mutant β-glucosidases, compositions and methods will now be more specifically described by Examples, but this disclosure is not limited thereto.

Reference Example 1

Preparation of Recombinant Expression of Parent β-glucosidase by *Escherichia coli*

A gene having the nucleotide sequence shown in SEQ ID NO: 2 of parent β-glucosidase was entirely synthesized and was ligated to the NcoI and BamHI sites of pET-11d using Ligation High (TOYOBO Co., Ltd.) to be transformed into JM109 (Takara Bio Inc.). Screening was performed using an LB agar medium containing ampicillin as an antibiotic. The produced vector pET-PfuBGL was isolated from the transformed JM109 strain with a miniprep kit (Qiagen N.V.) and was subjected to nucleotide sequence analysis. The pET-PfuBGL was transformed to an *Escherichia coli* BL21(DE3) pLysS strain for expression to prepare a BL21-PfuBGL strain. The BL21-PfuBGL strain was inoculated into 10 mL of an ampicillin-containing LB medium, followed by shaking culture (preculture) at 37° C. overnight. As the main culture, the bacterial body obtained by the preculture was inoculated into 1 L of an ampicillin-containing LB medium, and shaking culture was performed until OD 600, the absorbance at a wavelength of 600 nm, reached 0.8. Subsequently, isopropyl-1-thio-β-D-galactoside (IPTG) was added to the medium at a final concentration of 0.4 mM, followed by further culture at 25° C. overnight. After the culture, the bacterial body were collected by centrifugation and resuspended in a 50 mM tris-HCl buffer (pH 8.0). The resulting solution was subjected to ultrasonic disintegration under cooling with ice, and the supernatant was collected by centrifugation as a cell-free extract. The resulting cell-free extract was kept warm at 85° C. for 15 minutes to flocculate and precipitate *Escherichia coli*-derived proteins other than the glucosidase. The sediment by centrifugation was removed, and the supernatant was dialyzed against a 50 mM acetate buffer (pH 5.0) with a dialysis membrane made of regenerated cellulose having a molecular weight cut-off of 10000 (manufactured by Spectrum Laboratories, Inc.). The resulting protein solution was used as parent β-glucosidase. The amino acid sequence of the resulting parent β-glucosidase is shown in SEQ ID NO: 1.

Example 1

Specification of Tetramer Formation Site of Parent β-glucosidase

The X-ray crystal structure of parent β-glucosidase (*Pyrococcus furiosus*) has been already reported (Thijis K. et al., Biochem., vol. 39, No. 17 (2000)), but the resolution was low, 3.3 Å, and the parent β-glucosidase is not registered in Protein Data Bank (PDB). Accordingly, to determine the three-dimensional structure of PfuBGL, X-ray crystal structure analysis was performed. Novel crystallization conditions were searched, and crystallization was successfully achieved using phosphoric acid as a precipitant. An X-ray diffraction experiment was performed in a large synchrotron radiation experimental facility SPring-8, and the structure of PfuBGL was determined with a resolution of 2.5 Å. The structure was determined by a molecular replacement method using, as a model molecule, the β-glycosidase (ThAggBGY, PDB ID: 1 QVB) having the amino acid sequence shown in SEQ ID NO: 22 derived from *Themosphaera aggregans*. The resulting three-dimensional structural data was used for analyzing interaction between subunits with software CCP4_Contact for structural analysis. A ribbon model obtained by the analysis is shown in FIG. 1. A homotetramer formed by interactions between subunits A and B and between subunits A and C was confirmed (FIG. 1). The interaction between subunits A and B given by the analytical results is summarized in Table 1.

TABLE 1

| | Subunit A (amino acid atom) | Subunit B (target amino acid atom) | Bond length(Å) | Binding mode |
|---|---|---|---|---|
| 1 | Arg 170 (NH1) | Leu166 (O) | 3.26 | Hydrogen bond |
| 2 | Arg 170 (NH2) | Asp169 (OD2) | 2.68 | Hydrogen bond |
| 3 | Arg 220 (NH1) | Arg220 (O) | 3.29 | Hydrogen bond |
| 4 | Arg 220 (NH2) | Gly44 (O) | 3.19 | Hydrogen bond |
| 5 | Tyr 227 (OH) | Lys165 (O) | 2.65 | Hydrogen bond |
| 6 | Phe 230 (N) | Glu39 (OE1) | 2.96 | Hydrogen bond |
| 7 | Glu 39 (OE1) | Phe230 (N) | 2.6 | Hydrogen bond |
| 8 | Ser 43 (O) | Arg220 (NE) | 3.39 | Hydrogen bond |
| 9 | Gly 44 (O) | Arg220 (NE) | 3.39 | Hydrogen bond |
| 10 | Gly 44 (O) | Arg220 (NH2) | 3.49 | Hydrogen bond |
| 11 | Lys 165 (O) | Tyr227 (OH) | 2.92 | Hydrogen bond |
| 12 | Leu 166 (O) | Arg170 (NH1) | 3.03 | Hydrogen bond |
| 13 | Asp169 (OD2) | Arg170 (NH2) | 2.79 | Hydrogen bond |
| 14 | Ser 229 (OG) | Lys 165 (NZ) | 3.54 | Hydrogen bond |
| 15 | Arg 170 (NH2) | Asp 169 (OD2) | 2.68 | Ionic bond |
| 16 | Asp 169 (OD2) | Arg 170 (NH2) | 2.79 | Ionic bond |

Figure 2:
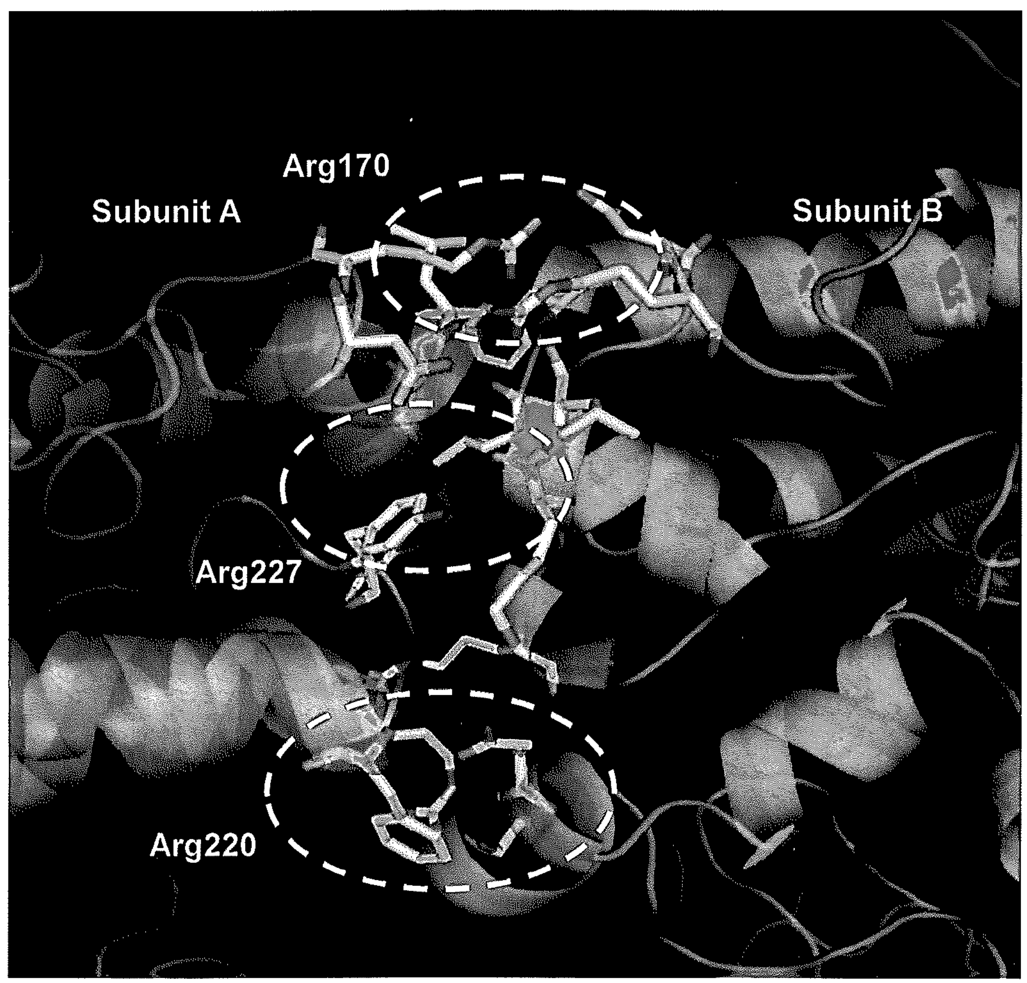
FIG. 2 is an enlarged ribbon model of the interaction site between subunits A and B of the parent β-glucosidase.

Among the interactions between subunits, those via only a nitrogen atom (N) and oxygen atoms (O) of the main chains of amino acids (amino acids indicated by italic letter) cannot be used for modification, because they have similar structures similar to any other amino acid. Accordingly, we believe that to modify the interaction between subunits, introduction of a mutation of an amino acid having a side chain participating in interaction, i.e., Glu39, Asp169, Arg170, Arg220, Tyr227, or Glu330, is effective. In particular, the bond between Arg170-Asp 169 is an ionic bond and is therefore strong compared to interaction due to other hydrogen bonds, and introduction of mutation thereto is assumed to be highly effective. FIG. 2 shows an enlarged ribbon model of the interaction site between subunits A and B. In particular, in Arg170, Arg220, and Tyr227 residues, the interface areas are large, and the bond lengths are short. Accordingly, they are believed to be ideal as a site to which mutation is introduced.

Example 2

Preparation of Mutant

Our β-glucosidase (mutant) was prepared by the following procedure using the primers shown in Table 2.

TABLE 2

| Mutated site | Nucleotide sequence (5'→3') | SEQ ID NO |
|---|---|---|
| Arg170Phe(Fw) | CAATTGCAGTAAGGAAACTTGGCCCGGATGCGGCTCCTGC | SEQ ID NO 3 |
| Arg170Phe(Rv) | GCAGGAGCCGCATCCGGGCCAAGTTTCCTTACTGCAATTG | SEQ ID NO 4 |
| Arg220Ala(Fw) | GGTTACATTAATCTAGCTTCAGGATTTCCACCAGG | SEQ ID NO 5 |
| Arg220Ala(Rv) | CCTGGTGGAAATCCTGAAGCTAGATTAATGTAACC | SEQ ID NO 6 |
| Tyr227Phe(Fw) | GGATTTCCACCAGGATTTCTAAGCTTTGAAGC | SEQ ID NO 7 |
| Tyr227Phe(Rv) | GCTTCAAAGCTTAGAAATCCTGGTGGAAATCC | SEQ ID NO 8 |

An R170A mutant (SEQ ID NO: 16) was produced by site-directed mutagenesis of a gene encoding the amino acid sequence shown in SEQ ID NO: 1 using oligonucleotides having the nucleotide sequences of SEQ ID NOs: 3 and 4. Similarly, an R220A mutant (SEQ ID NO: 17) and a Y227F mutant (SEQ ID NO: 18) were produced using oligonucleotides having the nucleotide sequences of SEQ ID NOs: 5 and 6 and SEQ ID NO: 7 and 8, respectively. Furthermore, an R170A/Y227F mutant (SEQ ID NO: 19) was produced by mutagenesis of the R170A mutant using oligonucleotides having the nucleotide sequences of SEQ ID NOs: 7 and 8; an R170A/R220A mutant (SEQ ID NO: 21) was produced by mutagenesis of the R170A mutant using oligonucleotides having the nucleotide sequences of SEQ ID NOs: 5 and 6; and an R170A/R220A/Y227F mutant (SEQ ID NO: 20) was produced by mutagenesis of the R170A/R220A mutant using oligonucleotides having the nucleotide sequences of SEQ ID NOs: 7 and 8.

The resulting genes were each expressed in *Escherichia coli* in accordance with the procedure described in Reference Example 1. The amino acid sequences of the R170A mutant, R220A mutant, Y227F mutant, R170A/Y227F mutant, R170A/R220A mutant, and R170A/R220A/Y227F mutant are respectively shown in SEQ ID NOs: 9 to 14 (methionine as a start codon is not included). It was confirmed that the mutants were all expressed in *Escherichia coli* as heterologous proteins.

Example 3

Cellobiose Decomposition Activity of Mutant 1

The cellobiose decomposition activity of each mutant (our β-glucosidase) prepared in Example 2 was compared with that of the parent β-glucosidase prepared in Reference Example 1 in the following experiment. The enzymes prepared in Example 2 and Reference Example 1 were each added to a 10 mM cellobiose/50 mM acetic acid buffer as a substrate at a final concentration of 0.23 mg/mL, followed by enzyme reaction at 50° C. for 30 minutes. The cellobiose decomposition activity of each mutant is shown in Table 3 as a relative value to the glucose concentration (g/L), which is defined as 100%, generated by parent β-glucosidase at a temperature condition of 50° C.

TABLE 3

| Parent β-glucosidase | R170A mutant | R220A mutant | Y227F mutant | R170A/Y227F mutant | R170A/R220A mutant | R170A/R220A/ Y227F mutant |
|---|---|---|---|---|---|---|
| 100% | 100% | 100% | 100% | 100% | 100% | 100% |

It was confirmed that there was no difference in the activity at 50° C. between parent β-glucosidase and each mutant.

Example 5

Cellobiose Decomposition Activity of Mutant 2

The parent glucosidase and each mutant (our β-glucosidase) were measured for their cellobiose decomposition activities in the presence of cellulose-containing biomass. The cellulose-containing biomass used was prepared by treating rice straw with 5% dilute sulfuric acid at 150° C. for 10 minutes. A reaction solution was prepared by adding 10 mM cellobiose/50 mM acetic acid buffer to a suspension of 5 wt % cellulose-containing biomass. Each enzyme prepared in Example 2 and Reference Example 1 was added to this reaction solution at a final concentration of 0.23 mg/mL, followed by enzyme reaction at 50° C. for 30 minutes. The cellobiose decomposition activity of each mutant is shown in Table 4 as a relative value to the glucose concentration (g/L), which is defined as 100%, generated by parent β-glucosidase at a temperature condition of 50° C.

TABLE 4

| Parent β-glucosidase | R170A mutant | R220A mutant | Y227F mutant | R170A/Y227F mutant | R170A/R220A mutant | R170A/R220A/ Y227F mutant |
|---|---|---|---|---|---|---|
| 100% | 101% | 101% | 98% | 96% | 94% | 163% |

It was confirmed that there was almost no difference in the cellobiose decomposition activity in the presence of cellulose-containing biomass between the parent glucosidase and the R170A mutant, R220A mutant, Y227F mutant, and R170A/R220A mutant, whereas the activity of the R170A/R220A/Y227F mutant was notably higher than those of parent glucosidase and other mutants.

Example 6

Measurement of Molecular Weight of Mutant by Blue-native PAGE

Whether the parent β-glucosidase and our β-glucosidases, R170A mutant, R170A/R220A mutant, and R170A/R220A/Y227F mutant, form stable tetramers or not was investigated by blue-native PAGE.

Figure 3:
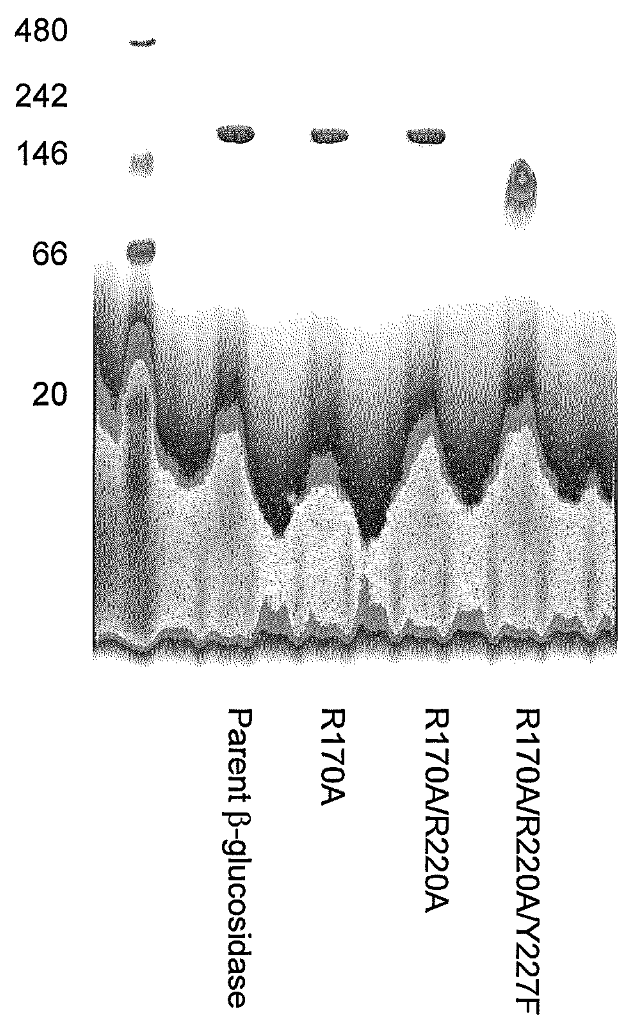
FIG. 3 shows the results of blue-native polyacrylamide gel electrophoresis (PAGE) of parent β-glucosidase and β-glucosidases introduced with mutation.

In the blue-native PAGE, 3-12% Native-PAGE Bis-Tris Gel (Invitrogen Corporation) was used. Electrophoresis samples were prepared by dissolving 1 μg of each of the parent β-glucosidase, R170A mutant, R170A/R220A mutant, and R170A/R220A/Y227F mutant in a sample buffer (50 mM imidazole (pH 7.0), 50 mM NaCl, 5 mM 6-aminohexanoic acid, 0.5% Coomassie G250, and 0.5% DDM). NativeMark protein standard (Invitrogen Corporation) was used as molecular weight markers. In the electrophoresis, 50 mM Tricine, 7.5 mM imidazole (pH 7.0), and Coomassie G250 were added to the anode side, whereas 25 mM imidazole (pH 7.0) was added to the cathode side. The electrophoresis was performed at a constant voltage of 150 V for 100 minutes. After fixation of bands, G-250 was decolorized. FIG. 3 shows a photograph of the resulting gel.

In the parent β-glucosidase, R170A mutant, and R170A/R220A mutant, the respective bands were detected at approximately the same positions between the molecular weight markers of 146 kDa and 242 kDa. Since the molecular weight of the parent β-glucosidase in a tetrameric form is 216 kDa, it was confirmed that these formed stable tetramers. On the other hand, the band of our R170A/R220A/Y227F mutant was detected between the molecular weight markers of 66 kDa and 146 kDa. That is, it was confirmed that the tetramer, which is originally formed by parent β-glucosidase, of our R170A/R220A/Y227F mutant was unstabilized and that the mutant was present in a trimeric or dimeric form in an aqueous solution.

Example 7

Hydrolysis of Cellulose-Containing Biomass Using Enzyme Composition for Decomposing Biomass, Containing β-glucosidase Enzyme compositions for decomposing biomass, composed of *Trichoderma reesei*-derived cellulase (Celluclast, Sigma-Aldrich Corp.) and glucosidase which was any of the parent glucosidase prepared in Comparative Example 1 and the R170A mutant, R170A/R220A mutant, and our R170A/R220A/Y227F mutant prepared in Example 2 were used. The enzymes were mixed such that the amount of cellulase was 0.5 mg/mL and the amount of each glucosidase was 0.005 mg/mL (1/100 of the cellulase amount).

The cellulose-containing biomass used was prepared by treating rice straw with 5% dilute sulfuric acid at 150° C. for 10 minutes. The hydrolysis was performed using a substrate prepared by suspending 5 wt % cellulose-containing biomass in 50 mM acetic acid buffer (pH 5.0) at 50° C. for up to 28 hours. The concentrations of generated glucose were measured.

TABLE 5

| | None | Parent β-glucosidase | R170A mutant | R170A/R220A mutant | R170A/R220A/Y227F mutant |
|---|---|---|---|---|---|
| Amount of generated glucose | 6 g/L | 8.3 g/L | 8.0 g/L | 8.6 g/L | 11 g/L |

It was confirmed that the amount of generated glucose was increased in the presence of glucosidase, compared to that in the absence of glucosidase. It was confirmed that the amount of generated glucose after the reaction for 28 hours of our R170A/R220A/Y227F mutant was higher than that in the reaction of the parent β-glucosidase, R170A mutant, or A170A/R220A mutant. In the absence of cellulose-containing biomass, there was no difference in the cellobiose decomposition activity among the R170A/R220A/Y227F mutant, parent β-glucosidase, R170A mutant, and A170A/R220A mutant (Example 3). Accordingly, it was confirmed that the activity of our mutant, the R170A/R220A/Y227F mutant, in the presence of cellulose-containing biomass was increased compared to that of the parent β-glucosidase.

Example 8

Crystal Structure Analysis of R170A/R220A/Y227F Mutant

Figure 4:
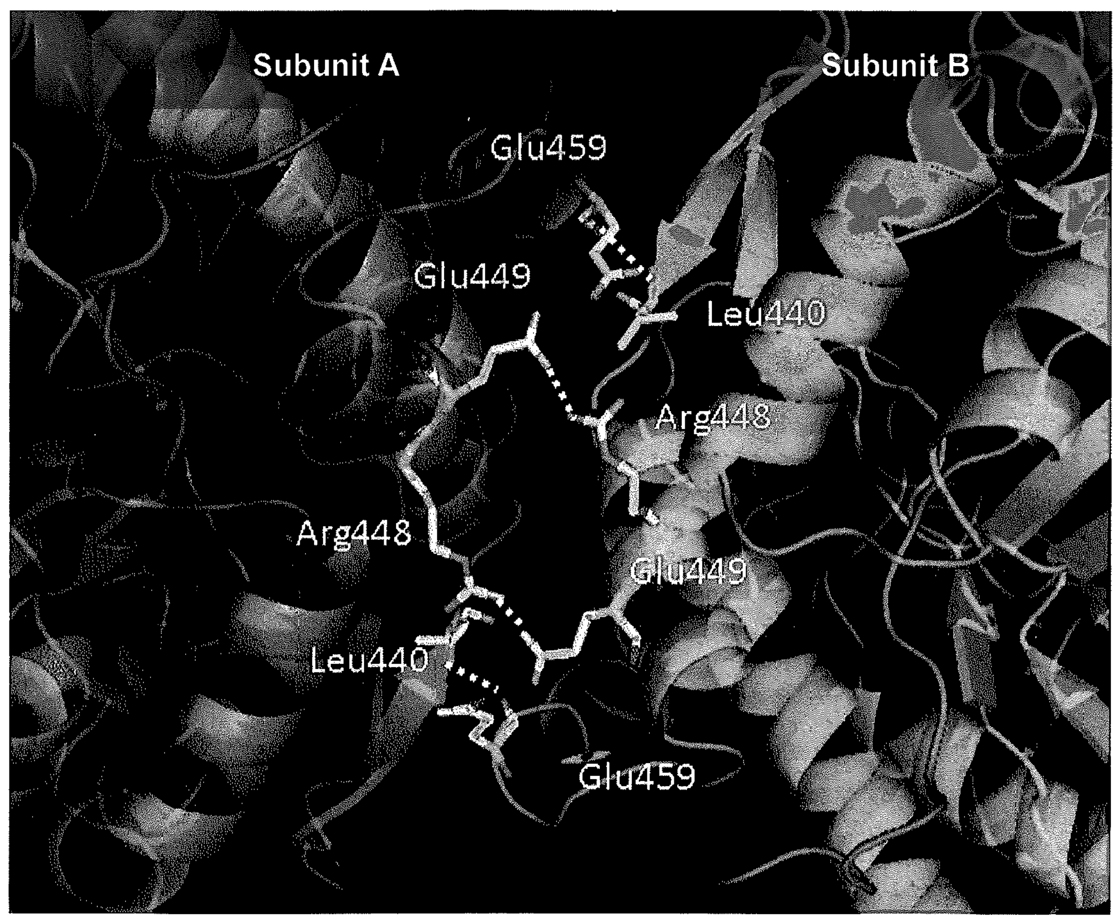
FIG. 4 is a ribbon model of a mutant β-glucosidase, obtained from the results of crystal structure analysis of the mutant β-glucosidase.
Figure 5:
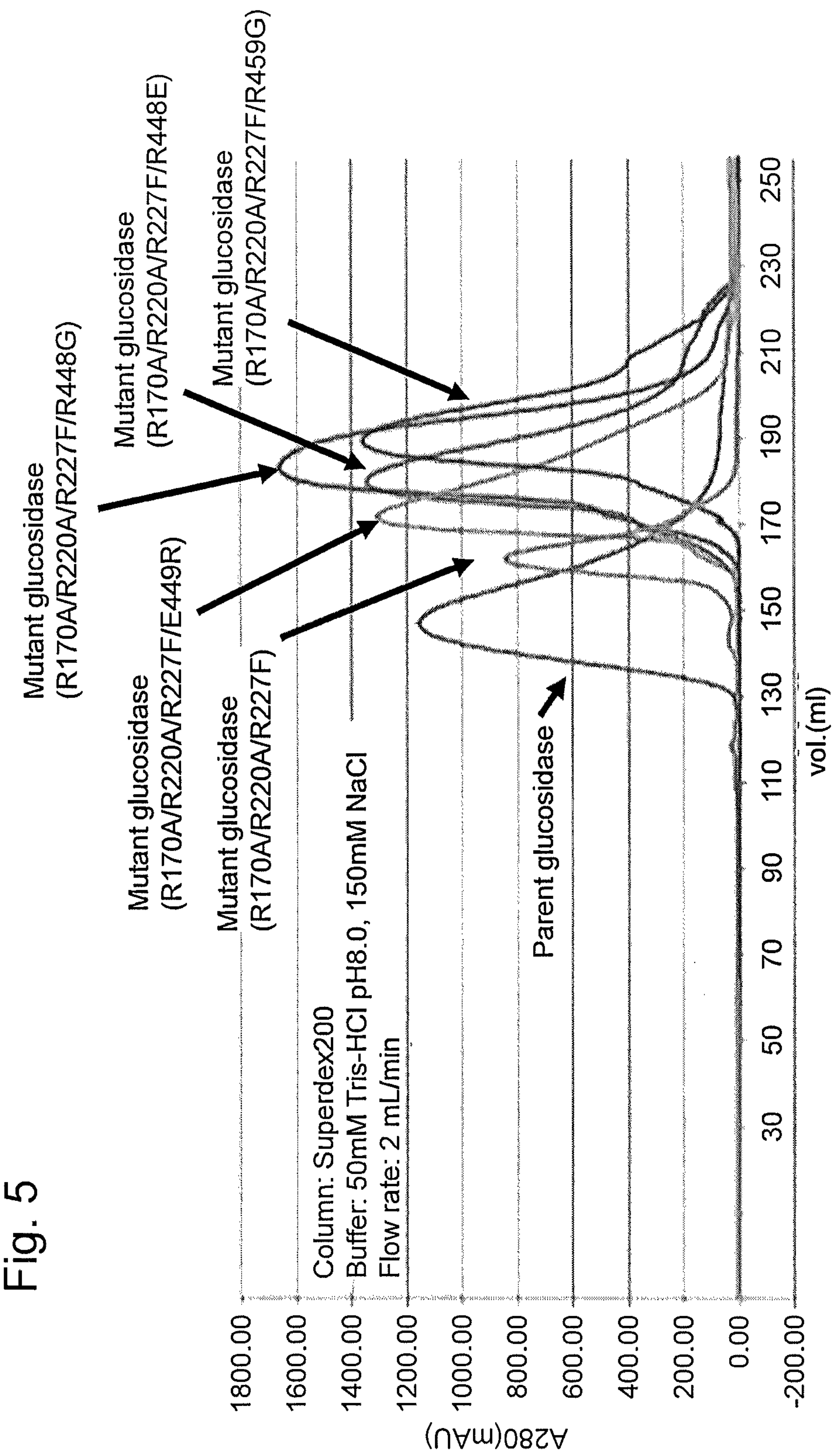
FIG. 5 shows the results of molecular weight measurement by gel filtration of the parent β-glucosidase and mutant β-glucosidases.

To determine the three-dimensional structure of the R170A/R220A/Y227F mutant, X-ray crystal structure analysis was attempted. Novel crystallization conditions were searched, and crystallization was successfully achieved using phosphoric acid as a precipitant. An X-ray diffraction experiment was performed in a large synchrotron radiation experimental facility SPring-8, and the structure of PfuBGL was determined with a resolution of 2.5 Å. The structure was determined by a molecular replacement method using, as a model molecule, the β-glycosidase (ThAggBGY, PDB ID: 1 QVB) having the amino acid sequence shown in SEQ ID NO: 22 derived from *Themosphaera aggregans*. The resulting three-dimensional structural data was used to analyze interaction between subunits with software CCP4_Contact for structural analysis. The ribbon model obtained by the analysis is shown in FIG. 4. It was confirmed that the R170A/R220A/Y227F mutant formed a homodimer by interaction between subunits A and C (FIG. 4). The interaction between subunits A and C given by the analytical results is summarized in Table 6.

TABLE 6

| | Subunit A (amino acid atom) | Subunit B (target amino acid atom) | Bond length(Å) | Binding mode |
|---|---|---|---|---|
| 1 | Arg 448 (NH2) | Glu 449 (OE1) | 2.54 | Hydrogen bond |
| 2 | Leu 440 (N) | Glu 459 (O) | 2.97 | Hydrogen bond |
| 3 | Glu 449 (OE1) | Arg 448 (NH2) | 2.49 | Hydrogen bond |
| 4 | Glu 459 (O) | Leu440 (N) | 2.84 | Hydrogen bond |

That is, it was revealed that the R170A/R220A/Y227F mutant forms a dimer by hydrogen bonds of amino acid residues: Arg448, Leu440, Glu449, and Glu459.

Example 9

Preparation of Mutant 2

Our mutant β-glucosidase (R170A/R220A/Y227F mutant) was revealed to form a dimer as shown in Example 8. Accordingly, whether the dimer can be modified to a monomer by further introducing mutation of at least one of Arg448, Glu449, and Glu459 into the R170A/R220A/Y227F mutant was investigated. The mutant gene was produced using the primers shown in Table 7 by the following procedure.

TABLE 7

| Mutated site | Nucleotide sequence (5'→3') | SEQ ID NO |
|---|---|---|
| Arg448Glu(Fw) | TTCGAGGAAATAGCCACTCAAAAAG | SEQ ID NO 23 |
| Arg448Glu(Rv) | TACCAGGGCGCTTGGCCTTAAATA | SEQ ID NO 24 |
| Arg448Gly(Fw) | TTCGGTGAAATAGCCACTCAAAAAGAA | SEQ ID NO 25 |
| Arg448Gly(Rv) | TACCAGGGCGCTTGGCCTTAAATA | SEQ ID NO 26 |
| Glu449Arg(Fw) | AGAAGGATAGCCACTCAAAAAGAAATTCCA | SEQ ID NO 27 |
| Glu449Arg(Rv) | TACCAGGGCGCTTGGCCTTAAATA | SEQ ID NO 28 |
| Glu459Gly(Fw) | GGATTAGCTCACCTCGCAGACCTC | SEQ ID NO 29 |
| Glu459Gly(Rv) | AATACCAGGGCGCTTGGCCTTAAATA | SEQ ID NO 30 |

The R170A/R220A/Y227F/R448E mutant (SEQ ID NO: 31), R170A/R220A/Y227F/R448G mutant (SEQ ID NO: 32), R170A/R220A/Y227F/E449R mutant (SEQ ID NO: 33), and R170A/R220A/Y227F/E459G mutant (SEQ ID NO: 34) genes were produced from the gene (SEQ ID NO: 20) of the R170A/R220A/Y227F mutant using oligonucleotides having the nucleotide sequences of SEQ ID NOs: 23 and 24, oligonucleotides having the nucleotide sequences of SEQ ID NOs: 25 and 26, oligonucleotides having the nucleotide sequences of SEQ ID NOs: 27 and 28, and oligonucleotides having the nucleotide sequences of SEQ ID NOs: 29 and 30, respectively.

Each of the resulting genes was expressed in *Escherichia coli* in accordance with the procedure described in Reference Example 1. The amino acid sequences of the R170A/R220A/Y227F/R448E mutant, R170A/R220A/Y227F/R448G mutant, R170A/R220A/Y227F/E449R mutant, and R170A/R220A/Y227F/E459G mutant are respectively shown in SEQ ID NOs: 35 to 38 (methionine as a start codon is not included). It was confirmed that the mutants were all expressed in *Escherichia coli* as heterologous proteins.

Example 10

Determination of Molecular Weight by Gel Filtration

The molecular weights of the parent glucosidase and the mutants were determined by gel filtration using HiLood 26/60 Suuperdex 200 as the column, a 50 mM tris-hydrochloride (pH 8) and 150 mM sodium chloride as the buffer. The enzymes prepared in Example 2, Reference Example 1, and Example 9 were each added to the column and eluted with the buffer at a flow rate of 2 mL/min. The enzyme was detected by measuring absorbance at 280 nm. Ovoalbumin (44 kDa), conalbumin (75 kDa), aldolase (158 kDa), and ferritin (440 kDa) were used as molecular weight markers, and a calibration curve was drawn based on the elution time of each enzyme component. The molecular weights measured by gel filtration (observed molecular weights: kDa) and molecular weights estimated from the amino acid primary structures (estimated molecular weights: kDa) are summarized in Table 8.

TABLE 8

| | Parent | mutant (R170A/R220A/Y227F) | | | | |
|---|---|---|---|---|---|---|
| | glucosidase | — | R448E | R448G | E449R | R459G |
| Observed molecular weight (kDa) | 237 | 129 | 70 | 63 | 92 | 50 |
| Estimated molecular weight (kDa) | 220 | 110 | 55 | 55 | 55 | 55 |

It was revealed that the observed molecular weight (237 kDa) of the parent glucosidase was almost equivalent to that of the tetramer and that the observed molecular weight (129 kDa) of the R170A/R220A/Y227F mutant was almost equivalent to that of the dimer. In the mutants prepared by further introducing mutation to the R170A/R220A/Y227F mutant, i.e., in the R170A/R220A/Y227F/R448E mutant, R170A/R220A/Y227F/E449R mutant, R170A/R220A/Y227F/R448G mutant, and R170A/R220A/Y227F/E459G mutant, the observed molecular weights were within a range of 50 kDa to 90 kDa, and it was estimated that these mutants were present completely in a monomeric form as an effect by further introducing the mutation.

Example 11

Cellobiose Decomposition Activity of Mutant 3

The parent glucosidase and each mutant (our β-glucosidase) were measured for their cellobiose decomposition activities in the presence of cellulose-containing biomass. The cellulose-containing biomass used was prepared by treating rice straw with 5% dilute sulfuric acid at 150° C. for 10 minutes. A reaction solution was prepared by adding 10 mM cellobiose/50 mM acetic acid buffer to a suspension of 5 wt % cellulose-containing biomass. Each of the enzymes, the R170A/R220A/Y227F/R448E mutant, R170A/R220A/Y227F/E449R mutant, R170A/R220A/Y227F/R448G mutant, and R170A/R220A/Y227F/E459G mutant, prepared in Example 9 was added to this reaction solution at a final concentration of 0.23 mg/mL, followed by enzyme reaction at 50° C. for 30 minutes. The cellobiose decomposition activity of each mutant is shown in Table 9 as a relative value to the glucose concentration (g/L), which is defined as 100%, generated by parent β-glucosidase at a temperature condition of 50° C.

TABLE 9

| Parent | mutant (R170A/R220A/Y227F) | | | |
|---|---|---|---|---|
| β-glucosidase | R448E | R448G | E449R | R459G |
| 100% | 179% | 183% | 197% | 197% |

It was revealed that the activities of the R170A/R220A/Y227F/R448E mutant, R170A/R220A/Y227F/E449R mutant, R170A/R220A/Y227F/R448G mutant, and R170A/R220A/Y227F/E459G mutant were highly increased compared to that of the parent glucosidase. It was also revealed that the activity of the mutant glucosidase (monomer) of Example 9 was higher than that of the R170A/R220A/Y227F mutant (dimer) of Example 5.

Industrial Applicability

Our β-glucosidase exhibits a high cellobiose decomposition activity in the presence of cellulose-containing biomass and can therefore be used in hydrolysis of biomass and production of a sugar solution.

All publications, patents, and patent applications cited in this specification are hereby incorporated by reference in their entirety.

The invention claimed is:

1. A mutant β-glucosidase comprising an amino acid sequence having a sequence homology of at least 90% to the amino acid sequence of SEQ ID NO: 1, wherein the amino acid sequence having a sequence homology of at least 90% comprises mutations of amino acids corresponding to at least three amino acids selected from the group consisting of glutamic acid at position 39, aspartic acid at position 169, arginine at position 170, arginine at position 220, tyrosine at position 227, and glutamic acid at position 330 in the amino acid sequence of SEQ ID NO: 1.

2. The mutant β-glucosidase according to claim 1, comprising an amino acid sequence having a sequence homology of at least 90% to the amino acid sequence of SEQ ID NO: 1, wherein the amino acid sequence having a sequence homology of at least 90% comprises substitutions of amino acids corresponding to at least three amino acids selected from the group consisting of glutamic acid at position 39, aspartic acid at position 169, arginine at position 170, arginine at position 220, tyrosine at position 227, and glutamic acid at position 330 in the amino acid sequence of SEQ ID NO: 1 with amino acids having neutral side chains.

3. The mutant β-glucosidase according to claim 2, wherein the amino acids having neutral side chains are selected from the group consisting of alanine, phenylalanine, and glycine.

4. The mutant β-glucosidase according to claim 1, comprising an amino acid sequence having a sequence homology of at least 90% to the amino acid sequence of SEQ ID NO: 1, wherein the amino acid sequence having a sequence homology of at least 90% comprises substitutions of amino acids corresponding to arginine at position 170, arginine at position 220, and tyrosine at position 227 in the amino acid sequence of SEQ ID NO: 1 with amino acids having neutral side chains.

5. The mutant β-glucosidase according to claim 4, wherein the amino acids having neutral side chains are selected from the group consisting of alanine, phenylalanine, and glycine.

6. The mutant β-glucosidase according to claim 1, comprising an amino acid sequence having a sequence homology of at least 90% to the amino acid sequence of SEQ ID NO: 1, wherein the amino acid sequence having a sequence homology of at least 90% comprises a substitution of an amino acid corresponding to arginine at position 170 in the amino acid sequence of SEQ ID NO: 1 with alanine; a substitution of an amino acid corresponding to arginine at position 220 in the amino acid sequence of SEQ ID NO: 1 with alanine; and a substitution of an amino acid corresponding to tyrosine at position 227 in the amino acid sequence of SEQ ID NO: 1 with phenylalanine.

7. The mutant β-glucosidase according to claim 1, comprising the amino acid sequence shown in SEQ ID NO: 14.

8. The mutant β-glucosidase according to claim 1, further comprising a mutation of an amino acid corresponding to at least one amino acid selected from the group consisting of leucine at position 440, arginine at position 448, glutamic acid at position 449, and glutamic acid at position 459 in the amino acid sequence of SEQ ID NO: 1.

9. The mutant β-glucosidase according to claim 8, comprising at least one substitution selected from the group consisting of a substitution of an amino acid corresponding to arginine at position 448 in the amino acid sequence of SEQ ID NO: 1 with an amino acid having a neutral side chain or an acidic side chain; a substitution of an amino acid corresponding to glutamic acid at position 449 in the amino acid sequence of SEQ ID NO: 1 with an amino acid having a neutral side chain or a basic side chain; and a substitution of an amino acid corresponding to glutamic acid at position 459 in the amino acid sequence of SEQ ID NO: 1with an amino acid having a neutral side chain or a basic side chain.

10. The mutant β-glucosidase according to claim 8, comprising an amino acid sequence shown in any one of SEQ ID NOs: 35 to 38.

11. An enzyme composition that decomposes biomass comprising the mutant β-glucosidase according to claim 1.

12. A method of producing a sugar solution from cellulose-derived biomass comprising contacting cellulose-containing biomass with the enzyme composition according to claim 11.

* * * * *